(12) United States Patent
Silver et al.

(10) Patent No.: US 6,197,254 B1
(45) Date of Patent: Mar. 6, 2001

(54) SELF-CONTAINED ASSAYING APPARATUS

(75) Inventors: Lawrence Stanley Silver, Hauppauge; Michael Juliano, East Setauket, both of NY (US); Adelbert M. Gillen, New Hope, PA (US)

(73) Assignee: International Food Protection, Bayport, NY (US)

(*) Notice: Subject to any disclaimer, the term of this patent is extended or adjusted under 35 U.S.C. 154(b) by 0 days.

(21) Appl. No.: 09/228,330

(22) Filed: Jan. 11, 1999

(51) Int. Cl.[7] .................................................... G01N 21/63
(52) U.S. Cl. ......................... 422/52; 422/58; 422/82.08; 250/351 C; 435/288.7; 436/169; 436/172
(58) Field of Search ..................... 436/169, 172; 435/288.7, 8; 250/361 C; 422/52, 82.08, 58

(56) References Cited

U.S. PATENT DOCUMENTS

| | | | |
|---|---|---|---|
| D. 401,369 | * 11/1998 | McClintock | D26/37 |
| 3,797,999 | 3/1974 | Witz et al. | 23/230 |
| 3,849,653 | 11/1974 | Sakaide et al. | 250/361 |
| 4,014,612 | 3/1977 | Atwood et al. | 356/88 |
| 4,495,416 | * 1/1985 | Mason | 250/338 |
| 4,672,039 | 6/1987 | Lundblom | 435/291 |
| 4,689,305 | 8/1987 | Stiffey et al. | 435/291 |
| 4,750,837 | 6/1988 | Gifford et al. | 356/417 |
| 4,800,580 | * 1/1989 | Houtman | 378/71 |
| 4,802,768 | 2/1989 | Gifford et al. | 356/417 |
| 4,804,845 | 2/1989 | Takeuchi | 250/367 |
| 4,818,883 | 4/1989 | Anderson et al. | 250/361 |
| 5,144,498 | * 9/1992 | Vincent | 359/885 |
| 5,166,755 | * 11/1992 | Gat | 356/419 |
| 5,188,965 | 2/1993 | Wannlund | 436/165 |
| 5,565,360 | 10/1996 | Lapota et al. | 435/286 |
| 5,580,785 | 12/1996 | Stiffey et al. | 435/288 |
| 5,580,791 | * 12/1996 | Thorpe | 436/62 |
| 5,783,399 | 7/1998 | Childs et al. | 435/7.2 |
| 5,798,263 | 8/1998 | Wood et al. | 435/288 |
| 5,811,251 | 9/1998 | Hirose et al. | 435/8 |
| 5,919,647 | * 7/1999 | Hiramatsu | 435/29 |

FOREIGN PATENT DOCUMENTS

| | | |
|---|---|---|
| 0025350 A2 | 3/1981 | (EP). |
| 0038134 B1 | 10/1985 | (EP). |
| 0238352 A2 | 9/1987 | (EP). |
| 0717840 B1 | 4/1998 | (EP). |
| 2089971 | 6/1982 | (GB). |
| WO 90/04775 | 3/1990 | (WO). |
| WO 94/17202 | 8/1994 | (WO). |
| WO98/49544 | * 11/1998 | (WO). |

* cited by examiner

*Primary Examiner*—Jill Warden
(74) *Attorney, Agent, or Firm*—Island Patent Associates

(57) ABSTRACT

A self-contained and highly portable assaying system includes a luminometer and a detector cap assembly. The detector cap assembly, which is structured with a first portion and a second portion, is capable of collecting a specimen, and causing a bioluminescent or chemiluminescent assaying reaction to be conducted in a light-tight environment within the detector cap assembly (devoid of any available ambient light). The luminometer is structured to be removably fixed to the detector cap assembly to sense low level luminescent emissions produced by the assaying reaction. A quantified result is subsequently provided to a user or operator that indicates the outcome of the assay activities.

50 Claims, 18 Drawing Sheets

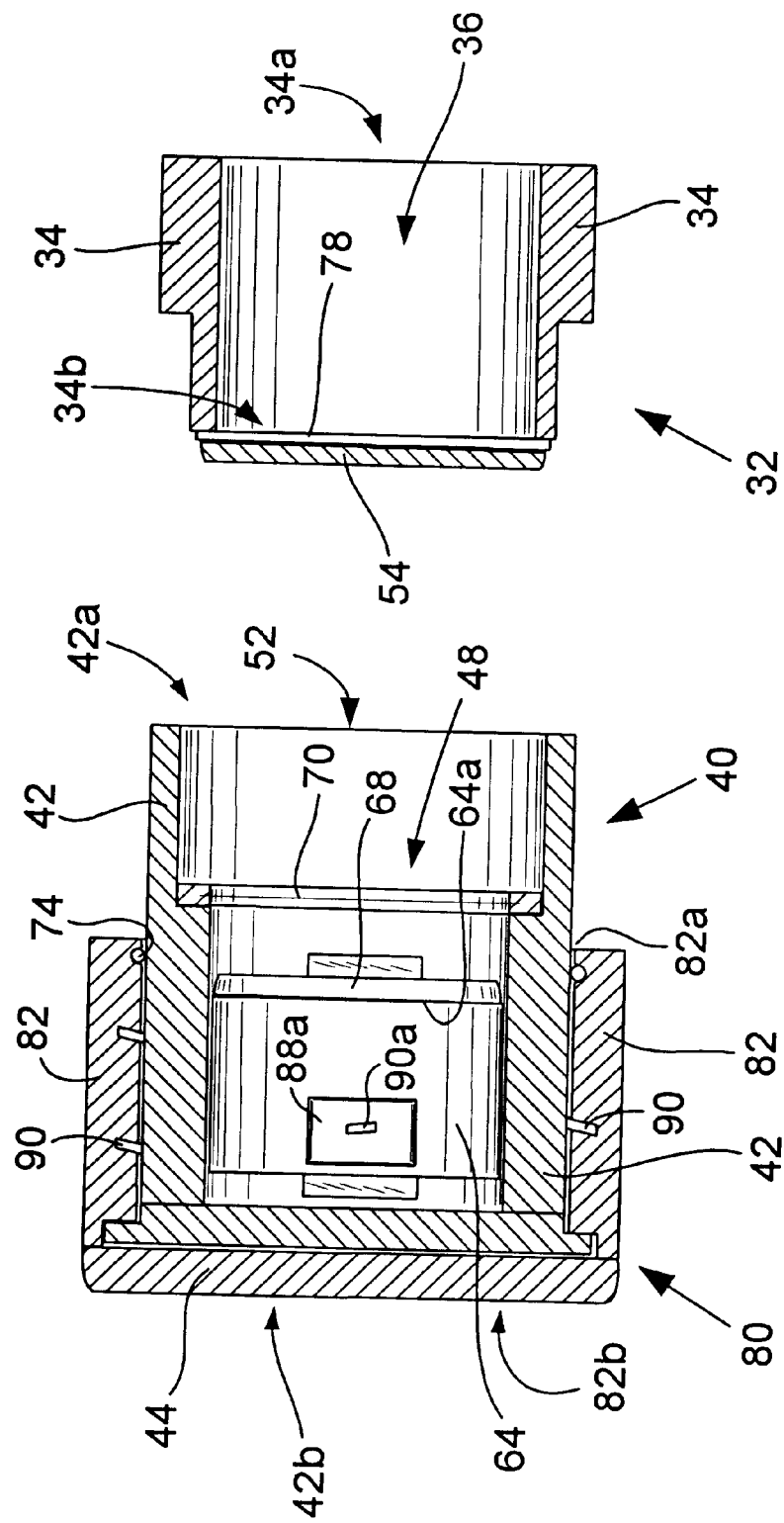

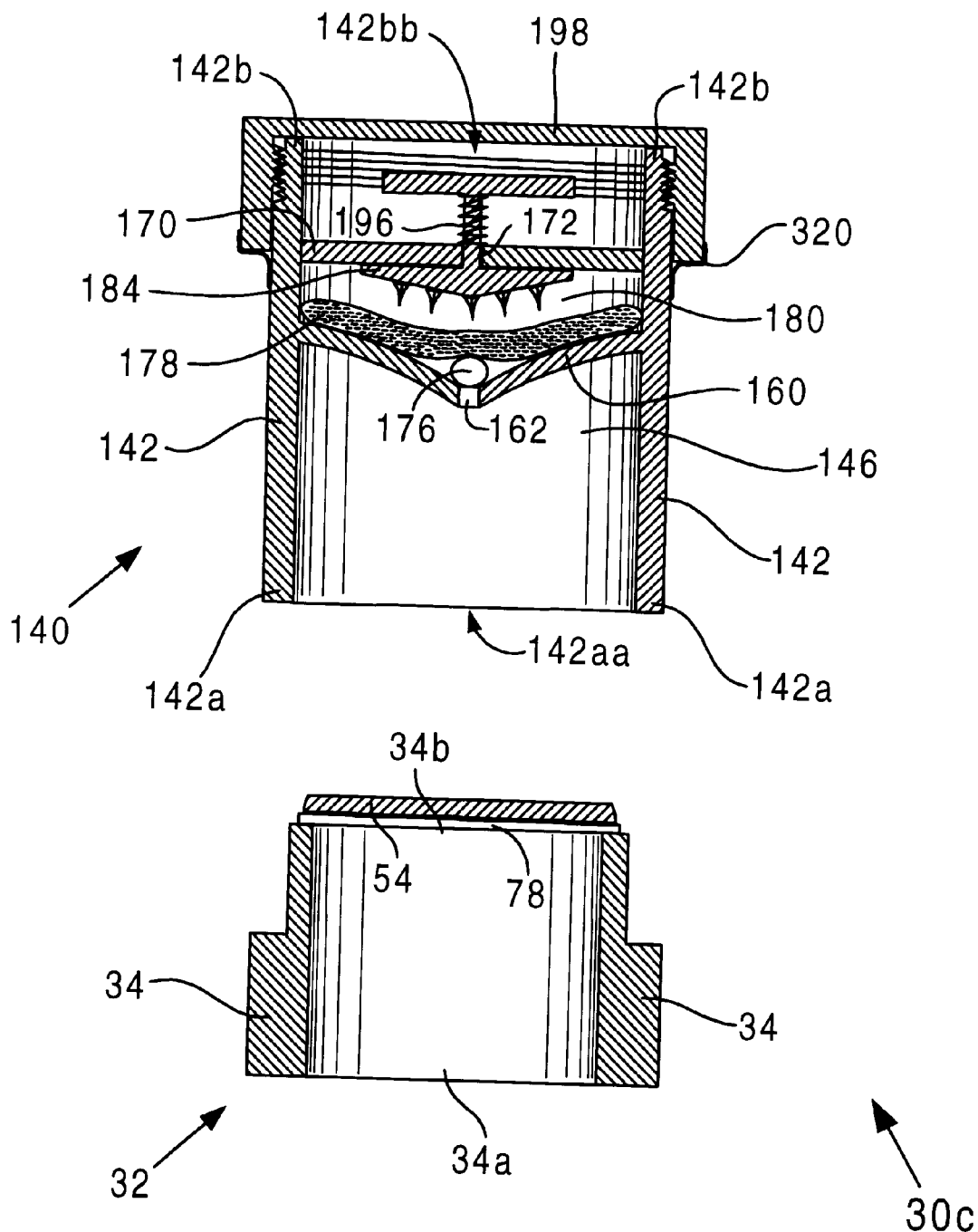

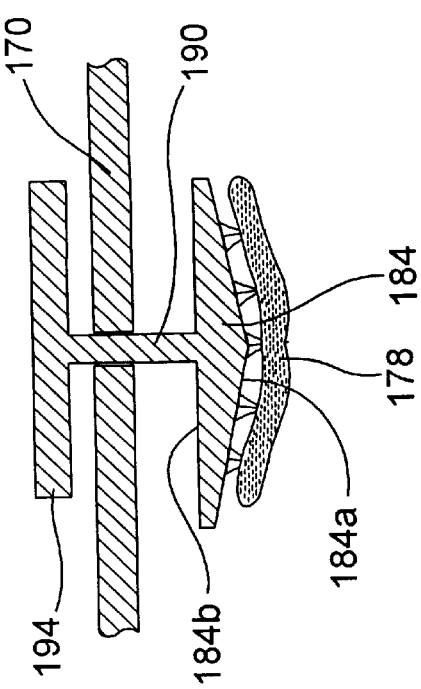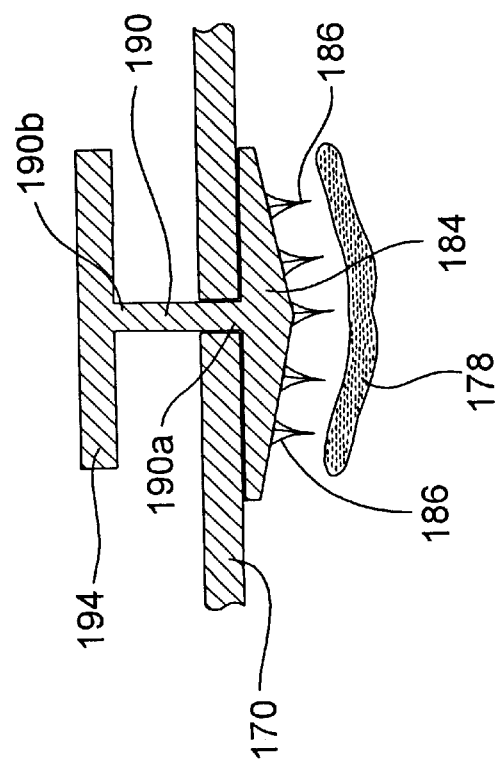

SELF-CONTAINED ASSAYING APPARATUS

BACKGROUND OF THE INVENTION

1. Field of the Invention

The present invention relates generally to assaying means and methods. More particularly, the invention relates to a self-contained and hand holdable assaying arrangement including a low level luminometer for detecting and quantifying low level luminescent emissions produced by a bioluminescent and or a chemiluminescent assaying reaction.

2. Description of the Prior Art

The production of light as a result of a chemical reaction is generally referred to as chemiluminescence. A chemiluminescent reaction usually produces product molecules in an electronically excited state. Such molecules return to a more stable state by the spontaneous emission of a photon, and hence, light is produced. If the reaction that produces light is biochemical, the phenomenon is referred to as bioluminescence.

A number of different species have developed the ability to emit light via bioluminescent reactions. These include, but are not limited to bacteria, fungi, fish, and insects. The luminescent materials from all organisms are termed luciferin, while the enzymes required for their conversion into a light signal are referred to as luciferase. Accordingly, these types of bioluminescent reactions are often termed 'luciferase-luciferin reactions'. The most extensively studied bioluminescent organism is the common American firefly, photinus pyralis. Although, the complete mechanism for the light producing reaction in the firefly has not been fully elucidated, it is been long understood that along with luciferin and luciferase other substances including magnesium ion, ATP (adenosine triphosphate) and molecular oxygen are required for the luminescence.

A particularly useful and interesting application involving bioluminescent reactions and their emissions involves the measurement of adenosine triphosphate (ATP), a material central to metabolism in virtually all living cells. As ATP is necessary for all living organisms to function, it serves as an excellent marker to indicate the presence of living matter (e.g., bacterial and other microbial matter). Accordingly, if one can ascertain (with a reasonable accuracy) a quantity of ATP present in a sample or specimen, either through direct or indirect measurement, one can make a determination of the quantity of microbes, microbial matter, or more generally the amount of analyte present. As discussed above, the most common method employed to measure the levels of ATP present involves the use of a firefly luciferase-luciferin assaying reaction. A properly conducted luciferase-luciferin reaction will produce detectable and measurable levels of luminescent emissions—even with relatively small quantities of analyte available. However, it must be understood that the level of luminescent emissions generated by such assaying reactions may be quite low, say as low as a tenth of a pico-watt (or less). The measurement of levels of emission this low necessitates sensitive accurate detecting and measuring systems that include low noise and generally specialized components.

There are many systems known and available that employ photomultiplier tubes (PMTs) and cooled charge-coupled devices (CCDs) to measure low level of emissions produced by bioluminescent and chemiluminescent assaying reactions. However, when considering PMT based devices, their cost is relatively high and they are easily damaged by shock and vibration. Further, as these devices require a high voltage supply and temperature stabilization for proper operation, they are rarely employed in low cost, highly portable instruments. CCD based devices can also be expensive, especially when structured to provide the necessary sensitivity. They are generally considered to have dark noise levels that are too high. As a consequence, when CCD devices are employed, they are almost always operated at a cooled, controlled temperature (which is generally well below the ambient temperature).

Alternative and generally low cost photo-sensing devices may be found in a number of solid-state (semiconductor) photodetectors including avalanche photodiodes, silicon-carbide photodiodes, PIN photodiodes, etc. Avalanche photodiodes, which are typically operated in a photo-conductive mode, have excellent bandwidth characteristics and good sensitivity. However, they exhibit a 'dark current' that is generally considered too high for very low level luminescent measurements, say at a 'sub' pico-watt level or less. Avalanche-photodiodes are also more expensive than other semi-conductor photodiodes, and as with PMTs, are often cooled to reduce their dark current noise levels. Other solid-state photodiodes, for example Silicon-carbide photodiodes, are not appropriate for ATP assay measurements as they have a peak sensitivity in the ultraviolet spectrum, say in the range of 200 to 380 nano-meters. PIN photodiode detectors have generally not been considered to be sensitive enough to use in low level ATP assaying luminometers. This is indicated by the fact that photomultiplier tube (PMT) devices, as well as CCD based systems, have been used almost exclusively in luminometers to measure such low level emissions.

As skilled persons will appreciate, a variety of devices and systems are available in the art to accurately determine and or compare relative and specific levels of light and luminescent emissions. These systems may be fundamentally separated into two categories: active and passive. Active systems employ one or more generally high level optical sources, such as lamps and or lasers. These systems may include beam splitting components, mirrors, and multiple detectors. Skilled persons would realize that the level of luminescent emissions detected with these active systems may actually be quite high. Accordingly, a number of the these systems may not be considered by skilled persons to be associated with the measurement of 'low-level emissions'.

In contrast, a passive system does not provide or include any lamps or other controlled light sources. These devices, which may be termed 'luminometers', are constructed with sensitive photo-detecting front ends that detect and measure the low level luminescent emissions of interest. These systems are generally bench or table top units, that are not highly portable and self-contained, and further, are relatively high cost units.

Assaying arrangements that employ bioluminescent assaying reactions to produce low levels of luminescent emissions require a means to collect a specimen or sample. Once a sample has been collected (say with a cotton tipped swab), the sample is assayed by exposure to suitable reagents and enzymes to cause the emissions-producing reaction to occur. The art provides many examples of luminometer apparatus that are employable in a lab or testing facility to measure emissions of an assaying reaction. However, these assaying arrangements are not provided in a self-contained and highly portable architecture. Therefore, such systems have not been usable, in the field. For example, if a cleanliness inspection is being conducted in a hospital or a restaurant's kitchen.

Skilled persons will therefore recognize the need for improved low level, self-contained and highly portable assaying apparatus. A most preferred apparatus would enable specimens to be collected, provide a suitable assaying enclosure, and quantify a volume of an analyte (of the specimen) by measuring relatively low level luminescent emissions produced by bioluminescent and or chemiluminescent assaying reactions associated with the assaying activities that are employed to investigate the specimen.

A full understanding of the present invention, including an understanding of a number of capabilities, characteristics, and associated novel features, will result from a careful review of the description and figures of several embodiments provided herein. Attention is called to the fact, however, that the drawings and descriptions are illustrative only. Variations and alternate embodiments are contemplated as being part of the invention, limited only by the scope of the appended claims.

SUMMARY OF THE INVENTION

In accordance with the present invention a self-contained and highly portable assaying apparatus includes a luminometer and a detector cap assembly. The luminometer is a self-contained hand-holdable unit for use in detecting and quantifying low levels of luminescent emissions produced by at least one of a bioluminescent and a chemiluminescent assaying reaction. These assaying reactions may also be simply termed a 'reaction'. Importantly, the low levels of luminescent emissions produced by the assaying reactions are generally proportional to the quantity of analyte (associated with or involved in the reaction). As such, an accurate measurement of the emissions enables a quantified assay of the analyte (or equivalently a volume thereof) to be determined. The luminometer includes a photodiode detector head assembly structured with a transparent window. The transparent window enables the luminescent emissions to enter the detector head assembly and be incident upon a photo detection means, which may most preferably include a PIN photodiode, to detect the level of the luminescent emissions. The luminometer further includes a computer operatively coupled to the photodiode detector head assembly to receive and process information provided therefrom to produce the quantified result indicative of the quantity of analyte associated with the assaying reaction (i.e., the 'system' under investigation).

A detector cap assembly of the assaying apparatus is structured to be removably fixed over the photodiode detector head assembly in a light tight manner so that the analyte (e.g., microbial matter) collected on a swabbing surface of the detector cap assembly is situated over (and proximate to) the transparent window and proximate to the photo detection means. An assaying reaction is then initiated (to investigate the system) in a light tight environment provided within the detector cap assembly, and emissions may be detected and measured. In preferable embodiments, the emissions are collected over a predetermined temporal interval. Once sufficient (luminescent) measurements have been made for a sufficient temporal interval, the quantified result may be provided to a user.

Preferred embodiments of the detector cap assembly may include a wall structure forming several chambers and or cavities. Importantly, each embodiment must have an architecture and required structure to provide a means to cause one of the bioluminescent and the chemiluminescent assaying reaction to occur within the detector cap assembly substantially upon an included swabbing surface. Therefore, when the detector cap assembly is installed on the photodiode detector head assembly, the luminescent emissions generated (preferably) upon the swabbing surface can be detected by the photo detection means to produce the quantified result indicating a volume of an analyte associated with the system under investigation.

The luminometer of the assaying apparatus may be embodied so that the level of luminescent emissions measured during the assaying reaction may be compared to a predetermined threshold level established to determine if a quantity of analyte is greater that a pre-determined quantitative limit (e.g., a health inspection safety limit).

A most preferred embodiment of the detector cap assembly is structured with a first portion and a second portion. The detector cap assembly is arranged to be removably fixed over a detector head housing of the luminometer. The second portion can then be separated from first portion, and the first portion can be used to collect a specimen or sample (of analyte) upon a swabbing surface. The second portion of the detector cap assembly may then be used to cover and cap the swabbing surface of the first portion to provide a light tight environment that is free of ambient light. An assay is then commenced wherein a level of luminescent emission is generated (by the assaying reaction), measured, and quantified.

The detector cap assembly may be provided in a large variety of differing arrangements. Several examples will be provided for preferred structures that employ dried reagents that are kept isolated from suitable wetting agents and other sources of moisture. It must be understood that the examples provided are illustrative and exemplary only. Further, it is contemplated that the luminometer of the present invention may also be employed with a variety of differing self-contained reaction vessels. These vessels may include those described hereinafter, as well as those having very simple structures utilizing simple cuvettes.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows:

FIGS. 5A, 5B, and 5C, provide a sectional side view of a first embodiment of a detector cap assembly of the present invention.

FIG. 9A illustrates yet another embodiment of the detector cap assembly shown in a sectional side view.

FIGS. 9B and 9C illustrate an embodiment of a perforation means in a first non-actuated position (FIG. 9B) and a second actuated position (FIG. 9C).

PARTIAL LIST OF REFERENCE NUMERALS

Figure 1:
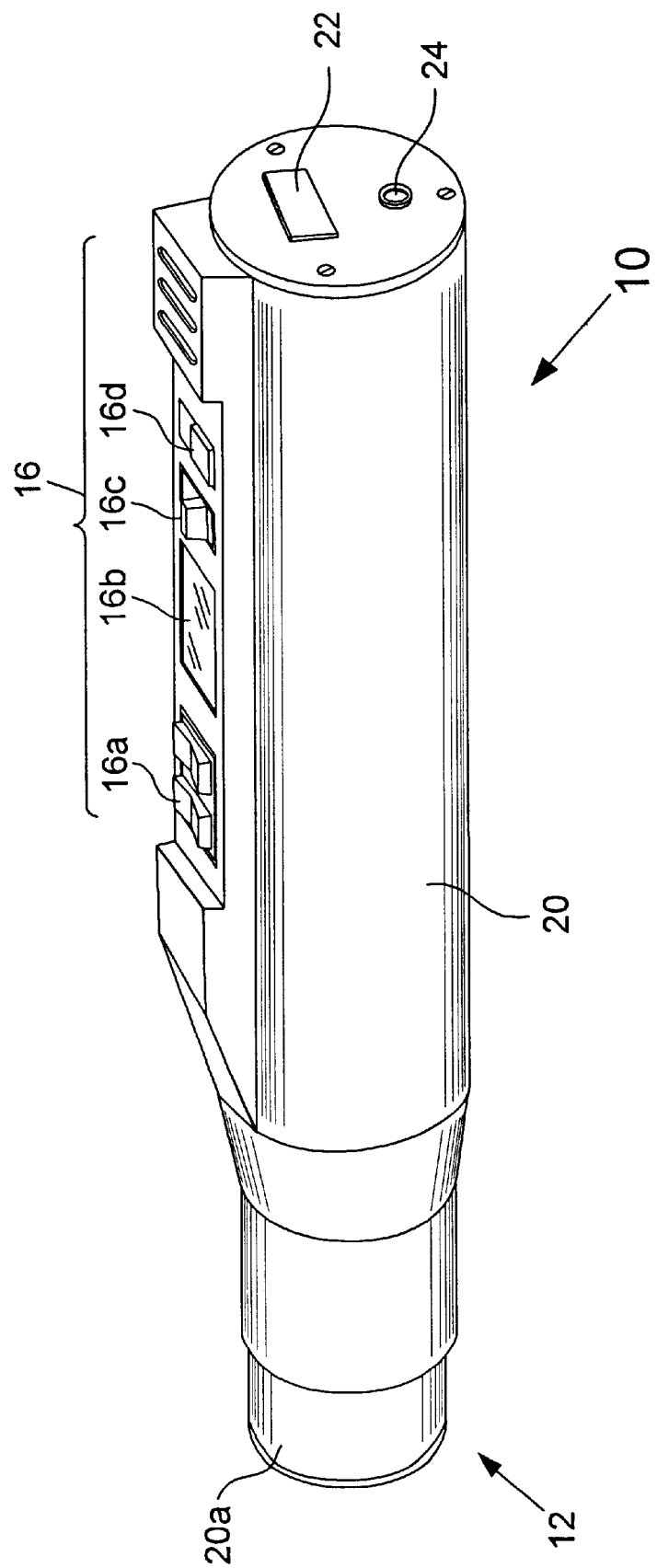
FIG. 1 illustrates a perspective view of an embodiment of a hand holdable luminometer in accordance with the present invention.

| | |
|---|---|
| 10 | luminometer |
| 12 | photodiode detector head assembly |
| 14 | (transparent or optical) window |
| 16 | user interface (including 16a, 16b, 16c, 16d, 16e) |
| 17 | current signal |
| 18 | electrical signal |
| 20 | housing |
| 20a | detector head housing |
| 22 | optical (IR) port |
| 24 | recharging connector |
| 26 | battery |
| 28 | power regulator |
| 28a | power coupling lines |
| 30 | detector cap assembly |
| 32 | first portion (of detector cap assembly 30) |
| 34 | wall structure of first portion |
| 34a | first opening of first portion |
| 34b | second opening of first portion |
| 36 | internal cavity of first portion |
| 40, 40' | second portion (of detector cap assembly 30) |
| 42, 42' | wall structure of second portion |
| 42a | first end of second portion |
| 42b | second end of second portion |
| 44, 44' | top (surface) of second portion |
| 46 | outer surface of wall structure 42' |
| 46a | threaded portion of outer surface |
| 48 | internal chamber of second portion |
| 52 | opening to internal chamber of the second portion |
| 54 | swabbing surface |
| 64, 64' | movable structure |
| 64a | flat surface of movable structure |
| 68 | porous pad |
| 70 | first barrier, or sealing means |
| 70a | support ring for first barrier |
| 72 | score lines |
| 74 | o-ring |
| 78 | second barrier |
| 80, 80' | cap-like portion |
| 82, 82' | wall structure of cap-like portion |
| 82a | first (open) end of cap-like portion |
| 82b | second (closed) end of cap-like portion |
| 84, 84' | top surface of cap-like portion |
| 86, 86' | interior surface of wall structure |
| 86a | threaded portion of interior surface of wall structure |
| 88 | slot in wall structure of second portion |

PARTIAL LIST OF REFERENCE NUMERALS—continued

| | |
|---|---|
| 88a | raised block |
| 90 | spiral groove |
| 90a | follower tab |
| 116 | circuit board (of luminometer 10/10a) |
| 118 | digital values (from analog-to-digital module) |
| 120 | electronic shutter |
| 124 | photodiode or semiconductor photodetector |
| 124a | PIN photodiode |
| 126 | photodetector package |
| 126a | chamber within photodetector package |
| 126b | base of photodetector package |
| 128 | thermoelectric cooler |
| 130 | pre-amplifier |
| 140 | second portion (alternate embodiment) |
| 142 | wall structure (of alternate embodiment) |
| 142a | bottom end (of wall structure 142) |
| 142b | top end (of wall structure 142) |
| 142aa | bottom opening |
| 142bb | top opening |
| 146 | cavity of second portion |
| 160 | first partition wall |
| 162 | hole(s) in first partition wall |
| 170 | second partition wall |
| 172 | hole in second partition wall |
| 176 | pellet(s) of dried reagent |
| 178 | fluid holding envelope |
| 180 | chamber (between first and second walls) |
| 184 | perforation disk |
| 184a | first surface of perforation disk |
| 184b | second surface of perforation disk |
| 186 | piercing points |
| 190 | shaft |
| 190a | first end of shaft |
| 190b | second end of shaft |
| 194 | button |
| 196 | spring, bias means |
| 198 | lid |
| 200 | signal conditioning module (means) |
| 210 | filter and amplification module |
| 220 | integrator |
| 230 | analog-to-digital module |
| 280 | power regulator |
| 300 | computer |
| 310 | control bus |
| 320 | safety locking means |
| 400 | result or results |

DETAILED DESCRIPTION OF THE INVENTION

It is important to establish the definition of a number of terms and expressions that will be used throughout this disclosure. The terms 'coupled', 'operatively coupled', and equivalents, are to be assumed to indicate the functional and or operational connection of one device or module to another, either directly or with one or more other devices or modules interposed. A functional or operational connection being required to deliver, receive, or more generally enable information including signals, data values, commands, etc., to be exchanged between one or more respective items, devices, or modules. Accordingly, the terms coupled and operatively coupled are to be considered synonymous, and somewhat broadly defined. The terms 'signal' and 'electrical signal', which are well known to skilled persons, may be provided by at least one suitable current and or voltage signal. The term 'luminometer', which is used extensively through out this disclosure, defines a means to measure low levels of luminescent emissions. Importantly, the luminometer of the present invention is embodied to provide a very portable, hand holdable, self-contained instrument that may be employed to measure said low level emissions when, for example, an assay is being conducted. The expression 'low level luminescent emissions', and similar expressions, are to be assumed to indicate levels of emissions typified by, for example, a luciferase-luciferin type of bioluminescent assaying reaction. Such an assaying reaction, as well as other known reactions, produce a correspondingly low level emission, say for example, in the range of one-hundredth of a pico-watt to tenths of a pico-watt. Such emissions are preferably within the visible light spectrum. The term 'analyte' is to be understood to encompass small microbes including, but not limited to, bacteria, viruses, other chemical moieties, and the like. Further, 'analyte' may be assumed to be singular or plural, as appropriate for the context in which it is used. The term 'wall structure' will be used primarily to refer to side walls of several portions of a detector cap assembly of the present invention. It should be understood that the term wall structure may be extended to include a top or end wall of a respective item being described, as determined by the context in which the term (wall structure) is applied. Other important terms and definitions will be provided, as they are needed, to properly and concisely define the present invention and its associated novel characteristics and features.

Figure 2:
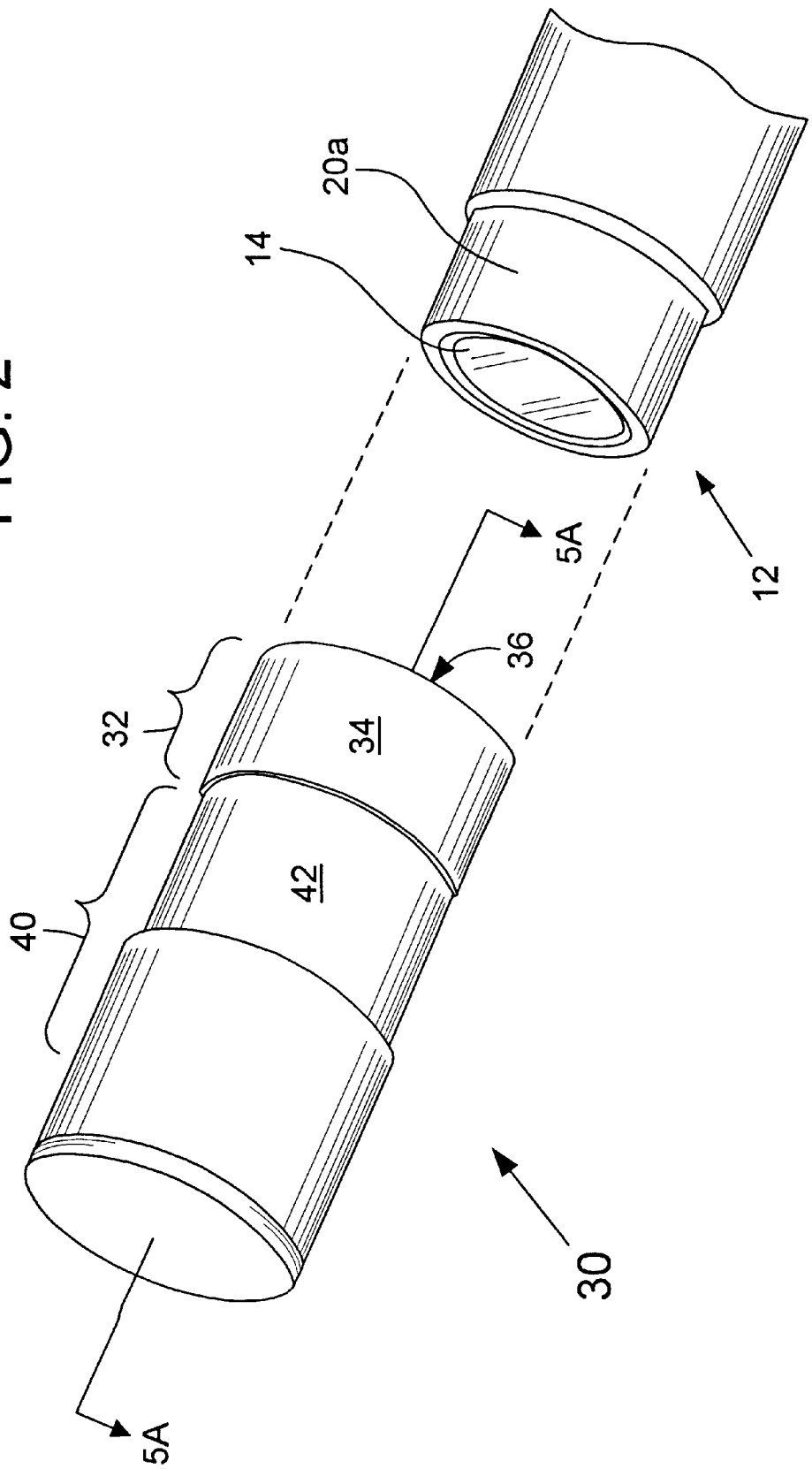
FIG. 2 depicts a perspective view of an embodiment of a detector cap assembly and a photodiode detector head assembly of the invention.

Referring now to FIG. 1, there is illustrated a therein a hand-holdable self-contained luminometer 10 for use in detecting and quantifying low levels of luminescent emissions. As can be seen, the luminometer 10 includes a photodiode detector head assembly 12 structured with a window 14. The transparent window 14, which is best seen in FIG. 2, enables the luminescent emissions to be detected by a suitable 'photo detection means' included within the photodiode detector head assembly 12. It should be noted that the photodiode detector head assembly 12 may be housed within the detector head housing 20a portion of the housing 20. However, many suitable arrangements of the housing 20, and the detector head housing 20a are possible.

The photodiode detector head assembly 12 provides at least one electrical signal representative the level of detected luminescent emissions. That is, one or more electrical signals are provided that are preferably proportional to the level of incident luminescent emissions passing through the window 14 and detected by the photodiode detector head assembly 12.

As will be discussed in greater detail below, the hand holdable housing 20 of the preferred embodiment is provided to house required electronic modules and components that may include a signal conditioning module and a computer. Accordingly, to be easily held and conveniently used to collect and assay specimens, a preferred elongated embodiment of the housing 20 has been depicted in FIG. 1. As shown, this embodiment is arranged with a narrowed detector head housing portion 20a having the photodiode detector head assembly 12 mounted therein. A user interface 16, which may be composed of items including rocker switches 16a, slide switches 16c, a display mean 16b, and or other well known user interface components, is provided to, among other things, enable information including a result to be delivered to a user or operator.

Turning now to FIG. 2, there is depicted therein an embodiment of a detector cap assembly 30 of the present invention. The detector cap assembly 30 is comprised of a first portion 32 and a second portion 40. The first portion 32 is configured having a wall structure 34 providing an internal cavity 36. As can be clearly seen in FIG. 5A (for example) the wall structure 34, which is preferably cylindrical, defines a first opening 34a and a second opening 34b. The first opening 34a and wall structure 34 of the first portion 32 are structured to enable the first portion 32 to be removably fixed over the photodiode detector head assembly 12 in a light tight manner, as can be clearly seen in FIGS. 3 and 5A. The expression 'light tight manner' is intended to mean that the first portion 32 will mate to the photodiode detector head assembly 12 so as to only enable luminescent emissions passing through the second opening 34b of the first portion 32 to be incident upon the window 14 (and a photodiode detection means situated behind said window). In a most preferred embodiment the first portion 32 will preferably install over (in a removably fixed fashion) the photodiode detector head assembly 12 such that at least a portion of the photodiode detector head assembly substantially fills the cavity 36 of the first portion 32 so as to position the window 14 of the photodiode detector head assembly 12 (as shown in FIGS. 6A) in close proximity to the second opening 34b of the first portion. Accordingly, this arrangement will minimize the distance between the photo detection means and a swabbing surface 54, as can be seen in FIG. 6A. This arrangement, wherein said distance is minimized, enables the low level emissions in accordance with the present invention to be readily detected when generated by a luminescent assaying reaction that is occurring on or within the swabbing surface 54.

Figure 3:
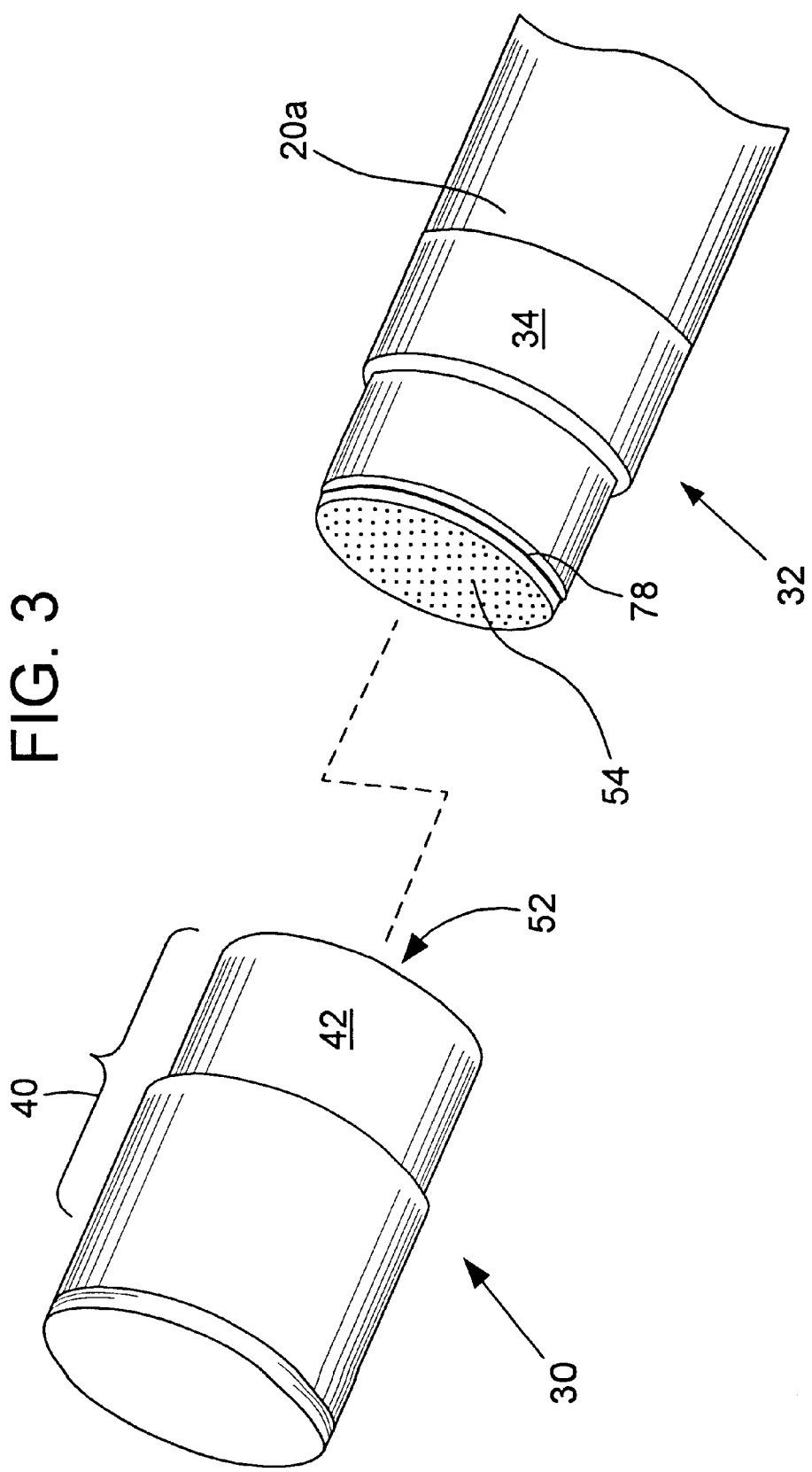
FIG. 3 provides a perspective view of the detector cap assembly of FIG. 2 with a first swabbing portion installed over a photodiode detector head assembly of the luminometer and ready to be used for swabbing and specimen collection.
Figure 4:
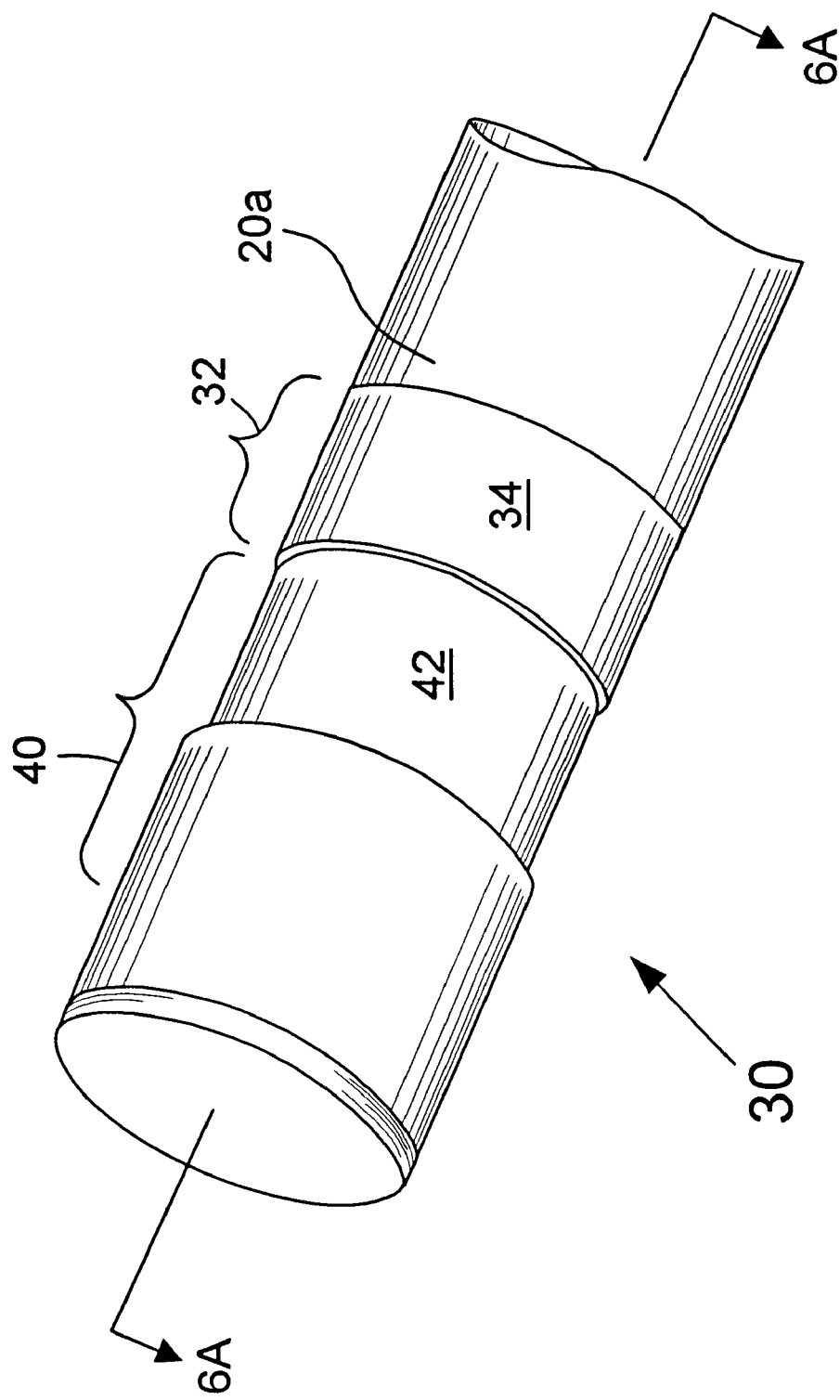
FIG. 4 illustrates the detector cap assembly of FIGS. 2 and 3, reassembled, and ready to be activated to conduct an assay.

Referring again to FIG. 2, it may be assumed that the detector cap assembly 30 may have been removed from a sealed, possible sterile, packaging arrangement (not explicitly shown). Once removed from the packaging arrangement, the detector cap assembly 30 may be installed over the photodiode detector head assembly 12 in the light tight manner (as shown in FIG. 4). Next, the second portion 40 is separated from the first portion 32. It may be noted that the second portion 40 may be coupled to the first portion 32 by a tether (not shown), or alternately, a hinge employed with a suitably structured first portion and second portion to enable the second portion to uncap the first portion and swing out of the way to expose the swabbing surface 54. As depicted in FIG. 3, the swabbing surface 54 is now exposed and available for swabbing of selected surfaces to, for example, collect microbial matter (i.e., the analyte to be investigated). In a preferred embodiment the swabbing surface 54 is provided as a substantially flattened and pre-wetted "bibulous" surface that is fixed to the first portion 32 of the detector cap assembly 30 and arranged to substantially cover the second opening 34b thereof. Accordingly, as shown, the swabbing surface 54 may be positioned, superposed over and essentially abutting the window 14 of the photodiode detector head assembly 12 when the first portion 32 is removably fixed over the photodiode detector head assembly 12 in the light tight manner. Once the selected surface has been swabbed (to collect analyte), the second portion 40 is re-installed over the first portion 32, as depicted in FIG. 4. Since the swabbing surface 54 is now covered by the second portion 40 in a light tight manner, ambient light is no longer incident upon the swabbing surface 54.

Figure 5A:
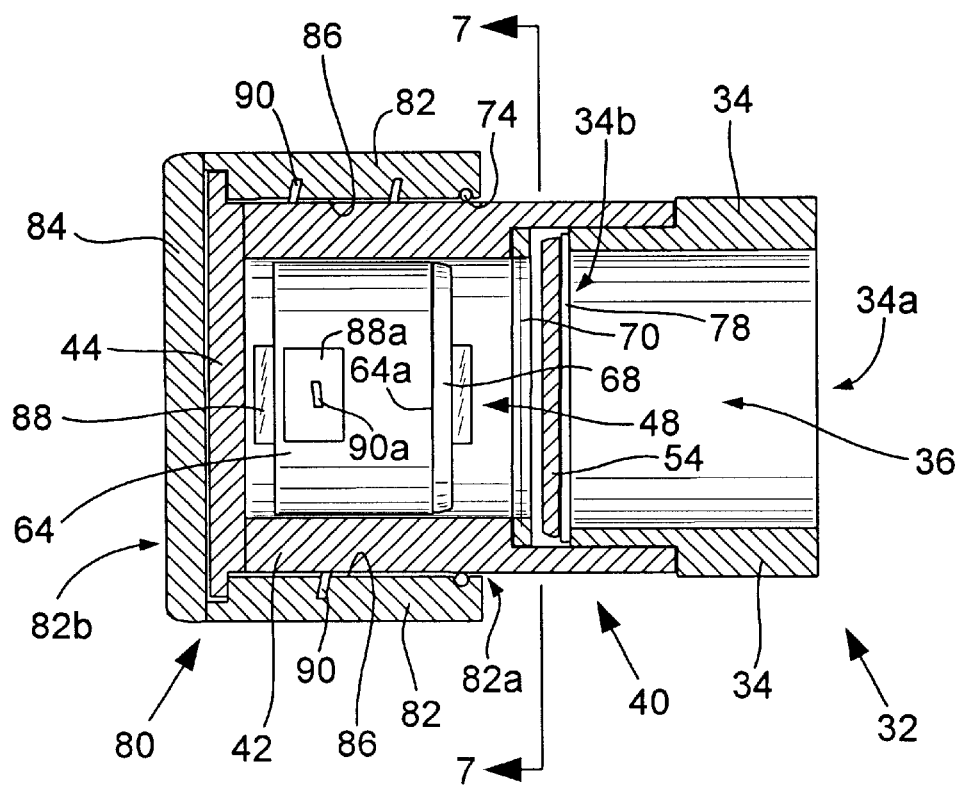
Figure 5B:
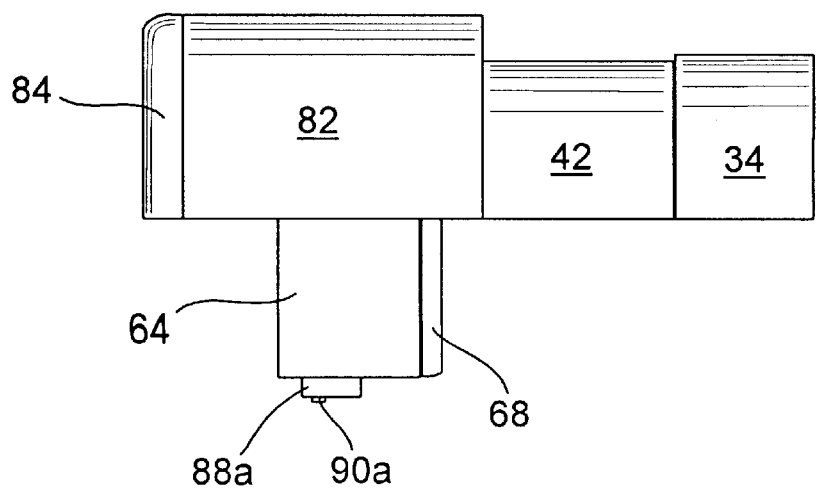
Figure 6A:
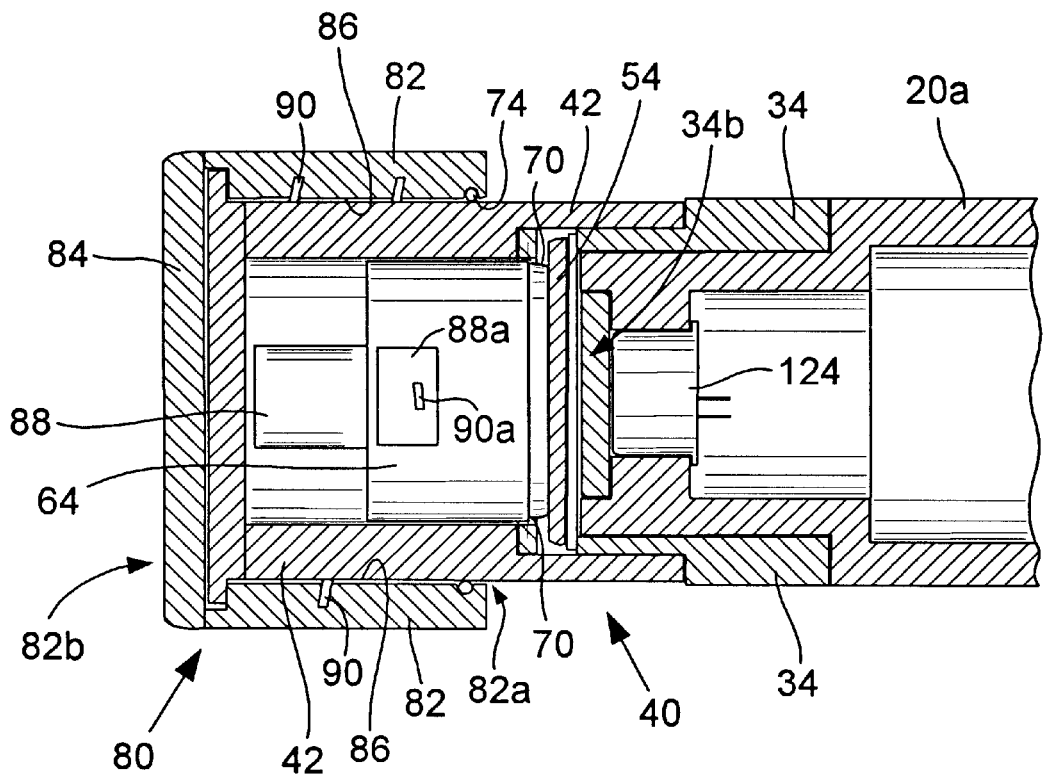
FIGS. 6A and 6B show the detector cap assembly of FIGS. 5A through 5C after being installed over an embodiment of the photodiode detector head assembly and actuated to commence assaying activities.

As can be seen in FIGS. 5A and 6A, the second portion 40 of the detector cap assembly 30 is structured having a wall structure 42 and a top surface 44. The wall structure 42 and the top surface 44 establish an internal chamber 48 and an opening 52 (as shown in FIG. 5C). The opening 52 shown in FIG. 5C is configured to enable the second portion 40 to be removably installed onto the first portion 32 so as to cover the swabbing surface 54 in order to cap the first portion 32 in the light tight manner. Therefore, the second portion 40 is installed onto and over the first portion 32 so as to substantially limit or prevent ambient light from being incident upon the swabbing surface 54. This need to cover or cap the swabbing surface 54 is essential to eliminate ambient light from being incident upon the swabbing surface 54 and the photo detection means of the detector head assembly 12 while the low level luminescent emissions of an assaying reaction are being detected and measured.

As shown in FIGS. 5A through 6B, the second portion 40 is configured to house a movable structure 64 within the chamber 48. The movable structure 64 is preferably embodied having a substantially flat surface 64a that is oriented proximate and parallel to the plane of the opening 52 of the second portion 40. The movable structure 64 is also configured to be movable between a first retracted position away from the opening 52 (as illustrated in FIG. 5A) and a second deployed position (as illustrated in FIG. 6A), which is more proximate to the opening 52. A porous pad 68 is fixed to and arranged to substantially cover the flat surface 64a of the movable structure 64. In the embodiments of the detector cap assembly 30 shown in FIGS. 5A through 6B, the porous pad 68 may be impregnated with suitable dried reagents that are activated by wetting when brought into pressure contact with the wetted swabbing surface 54 (as depicted in FIG. 6A). It should be noted that the term 'pressure contact' may be assumed to indicate that the porous pad 68 is brought into contact with the swabbing surface 54 with a sufficient pressure to enable the wetness of the swabbing surface 54 to wet and activate the dried reagents that impregnate the porous pad 68. The reagents will then dissolve and be drawn from the porous pad 68 to the swabbing surface 54. In a most preferred embodiment of the invention, when the analyte has been collected upon the swapping surface 54 and sufficient luciferase-luciferin dried reagents are employed to produce a luciferase-luciferin reaction, low level luminescent emissions will be produced. It may be noted that the expression "possibly resulting in one of either a bioluminescent and a chemiluminescent assaying reaction producing low level luminescent emissions" is intended to indicate that an assaying reaction will occur at a sufficient intensity, if an analyte (e.g., microbial matter) is present in a sufficient volume on the swabbing surface 54. Conversely, if a sufficient volume of analyte is not present, an assaying reaction will not provide emissions with a sufficient intensity to be detected and measured.

Figure 6B:
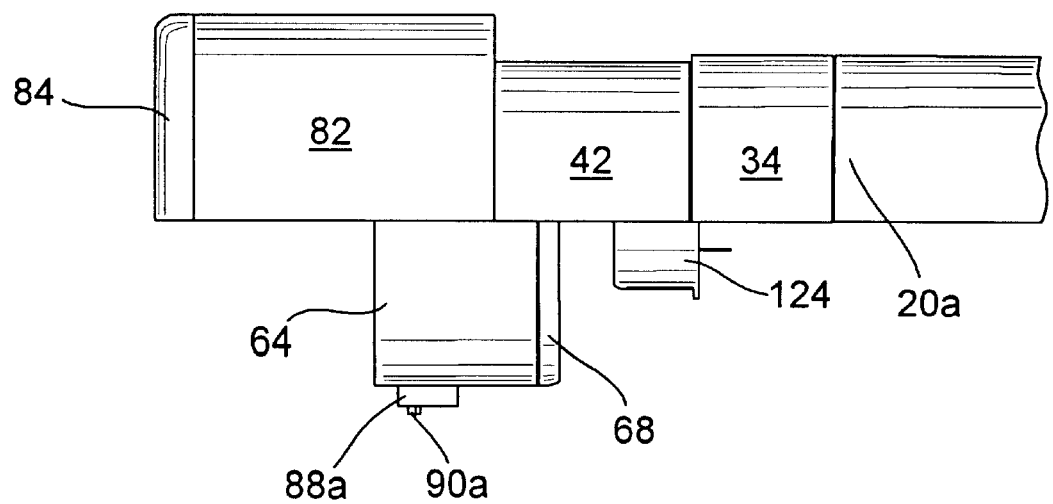

Skilled individuals will appreciate the need to prevent moisture and humidity from prematurely activating the dried reagents of the porous pad 68. Accordingly, a means is required to frangibly seal the internal chamber 48 until such time that the movable structure 64 is to be moved from the first retracted position to the second deployed position. Also, the means must be arranged to enable the suitable wetting of the porous pad 68 when the pressure contacting of the swabbing surface 54 and porous pad 68 occurs. Such a sealing or barrier means may be provided by a first barrier 70, which is structured to be thin and frangible. The first barrier 70 is arranged to cover the opening 52 of the second portion 40 in a recessed fashion, as illustrated is FIGS. 5A and 6A. A support ring 70a may be provided to support the frangible barrier 70, as illustrated. The arranging of the first barrier 70 in the recessed fashion enables a portion of the internal chamber 48 having the porous pad 68 contained therein to be hermetically sealed while the movable structure 64 is in the first retracted position. Thus, the hermetically sealed portion of the internal chamber 48 enables the porous pad 68 to remain dry while the movable structure 64 is maintained in the first retracted position. The recessed fashion of positioning the first barrier may also enable the photodiode detector head assembly (and the first portion 32) to be placed into the second portion without rupturing the first or frangible barrier. Accordingly, after swabbing has been completed, possibly causing analyte to be collected upon the swabbing surface 54, the second portion 40 may be re-installed over the first portion 32. The movable structure 64 including the porous pad 68 may next be moved from the first retracted position (FIG. 5A) to the second deployed position, as is shown in FIGS. 6A and 6B, causing the first barrier 70 to be ruptured.

Figure 7:
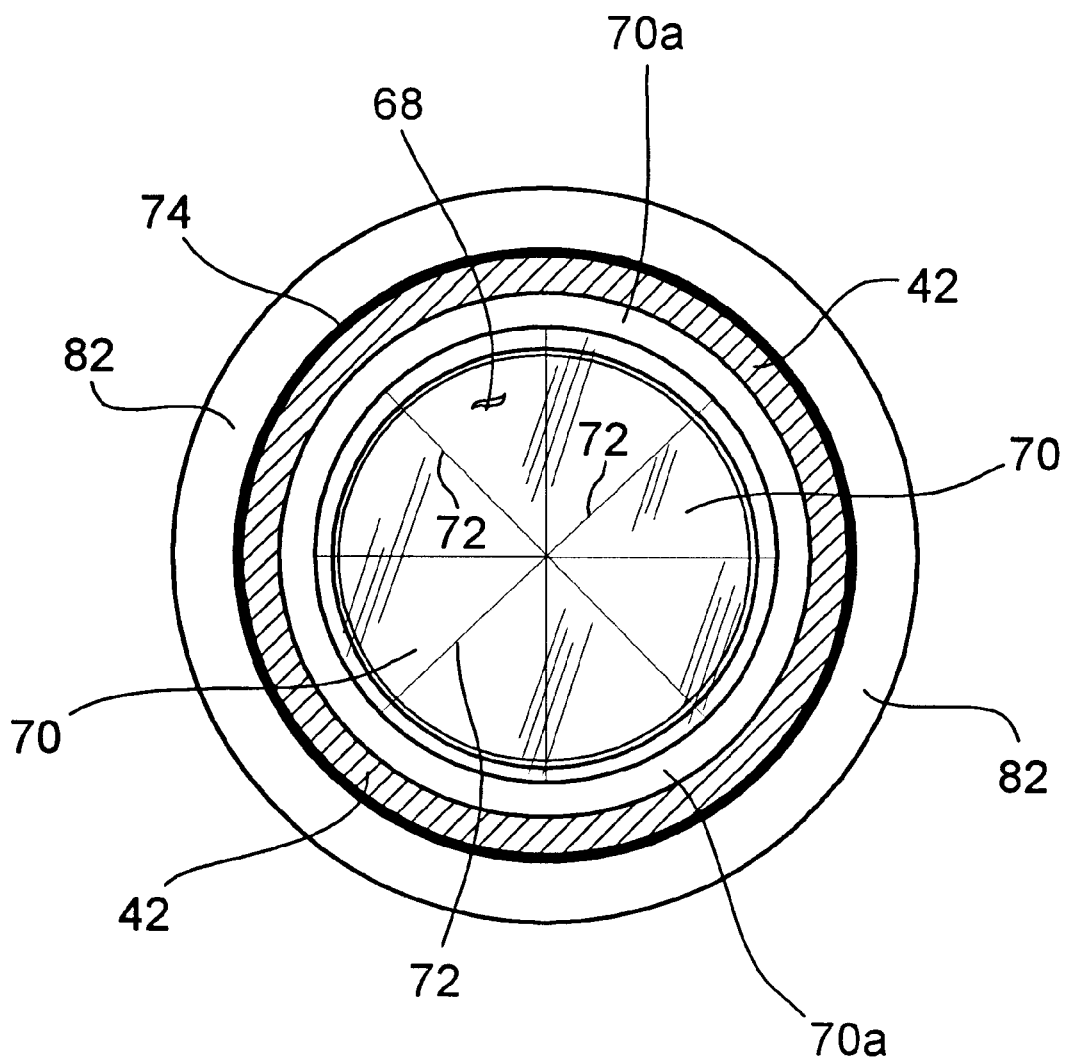
FIG. 7 illustrates a partially sectioned plan view of a portion of the detector cap assembly taken along a line 7—7 of FIG. 5A.

It should be noted that the first barrier 70 must be structured to be appropriately ruptured when the movable structure 64 is moved from the first retracted position to the second deployed position. The term 'appropriately rupturing' (and equivalents) are to be defined as rupturing in a suitable fashion so as to enable sufficient wetting agents of the swabbing surface 54 to wet the dried reagents of the porous pad 68 and cause a desired assaying reaction (when sufficient analyte is present). As shown in FIG. 7, the first barrier 70 may be scored with score lines 72 that are provided to establish rupture or tear locations to facilitate the appropriate rupturing of the first barrier 70. Further, if the first barrier 70 is provided by a stretched, possibly elastic material, the rupturing may result in a maximal direct contacting of the swabbing surface 54 and the porous pad 68 when the pressure contacting is established. As such, when the movable structure 64 is moved from the first retracted position to the second deployed position, the first barrier 70 is ruptured, the porous pad 68 is brought into pressure contact with the swabbing surface 54 causing the dried reagents to be dissolved, and drawn to and activated by the wetness of the pre-wetted swabbing surface 54. If an analyte is present on or in the swabbing surface, the activation of the dried reagents will result in at least one of a bioluminescent assaying reaction and or a chemiluminescent assaying reaction producing the low level luminescent emissions that are detectable by the photodiode detector head assembly 12 of the luminometer 10.

It is important to understand that in order to restrict ambient light from being incident upon the swabbing surface 54, the wall structures of the first and second portions, as well as portions of the housing of the luminometer 10 must be opaque, and as illustrated, suitably structured. Further, although said wall structures are preferably cylindrical in shape, other suitable and possibly preferable shapes and mechanical arrangements may be provided by skilled persons. As such, even though the photodiode detector head assembly 12 is illustrated as being cylindrical and shown to protrude from the housing 20 so that the detector cap assembly 30 may be snugly fit over the housing portion 20a (fixed there in the light-tight manner), many other arrangements are possible and contemplated. For example, the window 14 may be situated within a housing configuration providing a female bayonet mounting arrangement around the window. When considering this configuration, the detector cap assembly 30 may be arranged with a male bayonet structure which is arranged to mate to and engage a female bayonet structure, causing the removable fixing of the photodiode detector head assembly 12 to the housing 20, as required. Therefore, even though the illustrated embodiments of the present invention are depicted employing tapered and friction based engaging arrangements, other structures including bayonet structures and simple treading arrangements may be alternately employed.

Figure 8A:
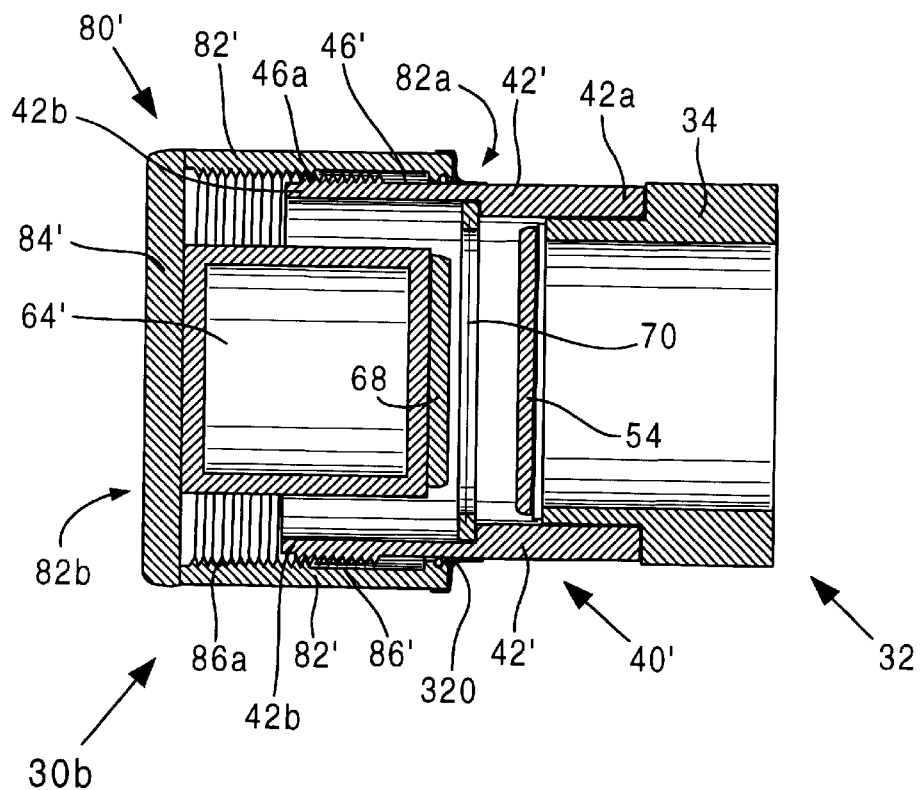
FIGS. 8A and 8B provide sectional side views of another embodiment of the detector cap assembly in accordance with the invention.

As illustrated in FIGS. 5A, 6A, and 8A, a transparent fluid impervious second barrier 78 may be provided under the swabbing surface 54 and over the second opening 34b of the first portion 32. The second barrier 78 may be included to seal the second opening 34b to prevent the transport of moisture therethrough. There are at least two situations where such a transport may occur. First, when the detector cap assembly 30 is not installed over the detector head housing 20a (i.e., over the photodiode detector head assembly 12), moisture may pass through the first opening 34a of the first portion 32 and possibly contaminate the swabbing surface 54. Alternately, when the movable structure 64 is moved to the deployed position (as shown in FIG. 6A), it is desirable to prevent the transport and loss of any of the wetting agent through the second opening 34b of the first portion 32. Therefore, when the second barrier 78 is omitted, the transport and loss of wetting agent may be controlled by the window 14 of the detector head assembly 12. However, as skilled persons would appreciate, the inclusion of the second barrier 78 prevents any contaminants, analyte, and or other microbial matter from passing from the swabbing surface 54 to the photodiode detector head assembly 12 or visa-versa.

A primary purpose for employing a (volume of a) wetting agent is to enable analyte to be easily collected, while also providing a means to wet the dried reagents of the porous pad 68. As skilled persons would appreciate, when considering appropriate wetting agents to employ, a volume of sterile water, a nucleotide releasing reagent, and or a variety of well known buffering agents may be used. The particular wetting agent may actually be determined as a function of the particular analyte to be detected or assayed, as well as the particular dried reagents employed to impregnate the porous pad 68. In addition, when considering preferred material suitable for providing the swabbing surface 54, known substances such as a cotton or a polymer pad may be selected. However, it should be noted that any substance which enables a sufficient volume of the wetting agent (say for example 0.1 to 1 ml) to be absorbed, and further enables the analyte to be collected during swabbing activities, may be employed. Similarly, when considering materials that may be employed to provide the porous pad 68 a number of known materials will suffice. However, a preferred material contemplated to embody the porous pad 68 include one or more layers of a (possibly paper) blotter material, a thin sponge-like material, and or one or more layers of a porous polymer sheet material.

Figure 8B:
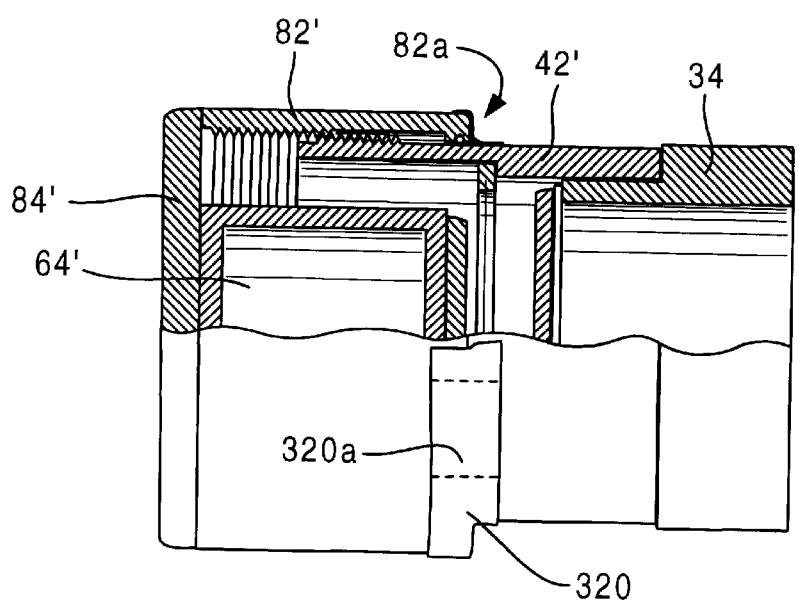

Returning to FIGS. 5A and 6A, one preferred embodiment of the present invention is structured with the second portion 40 that is comprising an outer cap-like portion 80, preferably having a cylindrical wall structure 82 (or a suitable wall structure that matches the shape of the second portion 40 of the detector cap assembly 30). An interior surface 86 of the wall structure 82 of the cap-like portion 80 may include a spiral groove 90 cut or formed therein. As can be seen, the cap-like portion 80 is coextensively and co-axially disposed over a second portion 40 and structured to be rotatably fixed thereto so as to rotate around a center (or a longitudinal) axis common to each of the outer cap-like portion 80 and the second portion 40. The wall structure 42 of the second portion 40 is configured having at least one slot 88 formed therein. The slot 88 may be arranged to form an essentially rectangular elongated opening, that is oriented parallel to, or along, the center axis of the second portion. The movable structure 64 of the detector cap assembly 30 of FIGS. 5A through 6B is preferably structured with a cylindrical shape having at least one raised block 88a that is sized to fit into and slide somewhat freely up and down the slot 88. An angled follower tab 90a extending radially from the raised block 88a extends through the slot 88 and is arranged to mate to and follow the spiral groove 90 of the cap-like portion 80. Accordingly, the movable structure 64 is configured to be movable from the first retracted position, as clearly seen in FIG. 5A, to the second deployed position, as clearly seen in FIG. 6A, by rotating the outer cap-like portion 80 with respect to the second portion 40. That is, as the outer cap-like portion 80 is rotated with respect to the second portion 40, the follower tab 90a causes the movable structure 64 to be moved from the first retracted position (away from opening 52 of the internal chamber 48 of the second portion 40) to the second deployed position (more proximate to the opening 52). This kind of structure, and equivalents thereof, that enable the movable structure 64 to be moved up and down the slot 88, are well known to skilled individuals and may be provided in a number of forms. As shown in FIGS. 5A and 8A, an o-ring 74 (or equivalent structures) may be included to maintain a hermetic seal of the portion of the interior chamber that houses the movable structure 64. A safety locking means 320 (and equivalent functional structures), as depicted in FIGS. 8A and 8B, may be included to prevent the cap-like portion 80 or 80' from inadvertently rotating (with respect to the second portion 40). The safety locking means (e.g., a securing band) may include perforations 320a to enable a user to easily and quickly remove the safety locking means 320. Skilled persons will recognize that other structures may be provided to realize the functional characteristics of the safety locking means 320.

Additionally, it should be noted that any suitable structure that enables a user to move the movable structure 64 from the first retracted position to the second deployed position, is contemplated as being within the scope of the present invention. For example, another embodiment of the detector cap assembly (30b) is illustrated in FIGS. 8A and 8B. The detector cap assembly 30b is arranged with an alternate structure to suitably move the movable structure 64 from the first retracted position to the second deployed position. As can be seen, the second portion 40' is comprised of an outer cap-like portion 80' having a preferably cylindrical wall structure 82' that is closed by a top surface 84' at a second (closed) end 82b. The first end 82a of the wall structure 82' of the cap-like portion 80' is open. The wall structure 82' is arranged with a threaded portion 86a that is provided on an interior surface 86' thereof. As shown in FIG. 8A and 8B, the threaded portion 86a of the interior surface 86' would preferably begin proximate to the second (closed) end 82b and extend a suitable distance (e.g., approximately halfway) down the height of the cap-like portion 80' along the interior surface 86'. The second portion 40' of the embodiment of FIGS. 8A and 8B is arranged (much like the second portion 40 of previously discussed embodiments) having its wall structure 42', and a first end 42a and a second end 42b. An outer surface 46' of the wall structure 42' of the second portion 40' is configured with a treaded portion 46a that is structured to mate to and engage the threaded portion 86a of the interior surface 86' of the outer cap-like portion 80'. The respective engaged threaded portions thereby enabling the outer cap-like portion 80' to move along a common center or longitudinal axis of each of the second portion 40' and the outer cap-like portion 80' when the outer cap-like portion 80' is rotated around said center axis with respect to the second portion 40'. This rotation effectively causes the outer cap-like portion 80' to be screwed coaxially and (at least partially) coextensively down and over the second portion 40'.

As is shown in FIGS. 8A and 8B, the top surface 84' of the outer cap-like portion 80' is structured with a movable structure 64' fixed to the top surface 84' and extending down into the second portion 40'. As such, and much like the movable structure 64 of the embodiment of FIGS. 5A through 6B, the movable structure 64' is movable from a first retracted position to a second deployed position when the outer cap-like portion 80' is rotated, and coaxially and coextensively screwed down over the second portion 40'. As discussed above, the movement of the movable structure 64' to the second deployed position will cause the frangible first barrier 70 to be ruptured, and effect the placement of the porous pad 68 in pressure contact with the swabbing surface 54.

Turning now to FIG. 9A, there is illustrated yet another embodiment of a detector cap assembly 30c depicted in a cross sectional view. The first portion 32 is equivalent to the first portion as shown and described in FIGS. 2 through 8B. A second portion 140 is structured having a vertical wall structure 142 and a top end 142b and a bottom end 142a. The second portion 140 is configured with a top opening 142bb at the top end 142b and a bottom opening 142aa at the bottom end 142a. The bottom opening 142a is, as discussed above, arranged to enable the second portion 140 to be removably installed onto the first portion 32 to cap the first portion and the swabbing surface 54 in the light tight manner.

The second portion 140 further includes a first partition wall 160 oriented substantially traverse to and preferably parallel with the bottom opening 142aa, and within the wall structure 142 of the second portion 140. The first partition wall 160 is suitably spaced from the bottom end 142a so as to form a cavity 146. The first partition wall 160 may be configured as depicted with a substantially concaved shape. A portion of the cavity 146 proximate to the bottom opening 142aa is filled by the first portion 32 when installed on the second portion 140. The first partition wall 160 further is provided with at least one hole 162. A second partition wall 170, which is preferably oriented substantially traverse to the top opening 142bb, and within the wall structure 142 of the second portion 140 so as to form a chamber 180 that is situated above the cavity 146. The second partition wall 170 is arranged with a hole 172. The function provided by the hole 172, or an equivalent arrangement will be discussed below. A sealed fluid holding envelope 178 is provided and situated in the chamber 180 to hold a volume of a suitable wetting agent. Also contained in the chamber 180 is at least one pellet 176 of dried reagent that is situated between the fluid holding envelope 178 and a top surface of the first partition wall 160. The pellets 176 are to be sized having a diameter greater than each hole 162 provided in the first partition wall 160 so that the pellets 176 not are easily moved through the respective holes 162 until they are at least partially dissolved by the wetting agents contained in the fluid holding envelope 178.

In order to activate the pellets 176 the fluid holding envelope 178 must be ruptured or perforated to release the (volume of) wetting agent contained therein. Accordingly, some perforation means, which is activated by a user, must be provided. For convenience the perforation means may be structured to be activated from a location proximate to the top opening 142bb, for example, above the second partition wall 170. It would also be desirable for said perforation means to be substantially housed within the chamber 180 and arranged to easily be actuated to perforate the fluid holding envelope 178 in order to release the volume of wetting agent into the chamber 180 to activate and dissolve the pellets 176. An embodiment of the perforation means, which is illustrated in FIGS. 9A, 9B and 9C, includes a perforation disk 184 located in the chamber 180 above the fluid holding envelope 178. The perforation disk 184 is structured with a first surface 184a and a second surface 184b (as best seen in FIGS. 9B and 9C). The first surface 184a is arranged with a plurality of piercing points 186 extending (downwardly) from the first surface and toward the fluid holding envelope 178. Preferably the first surface 184a is oriented substantially parallel to and spaced from the fluid holding envelope 178 when the perforation means is not actuated (as shown in FIG. 9B). A shaft 190 is included having a first end 190a and a second end 190b. The first end 190a is fixed to the second surface 184b of the perforation disk 184b so that the shaft 190 passes through the hole 172 in the second partition wall 170 with the second end 190b of the shaft 190 situated at the location proximate to the second opening 142bb, and above the second partition wall 170. Accordingly, the second end 190b of the shaft 190 may be employed to actuate the perforation disk 184, as depicted in FIG. 9C, to perforate the fluid holding envelope 178. In a preferred embodiment of the detector cap assembly 30c, a button 194 may be fixed to the second end 190b of the shaft 190 to assist in activating the perforation means. When the button 194 is used to depress the shaft 190, the perforation disk 184 is moved from a first position (as shown in FIG. 9B) to a second position (as shown in FIG. 9C). In the first position the perforation disk 184 is spaced from the fluid holding envelope 178 and the volume of wetting agent is sealed therein. It may be noted that the perforation disk 184 may be biased in the first position by the inclusion of a spring 196, which is shown in FIG. 9A. When the second end 190b of the shaft 190 is depressed to move the perforation disk 184 to the second position, the fluid holding envelope 178 is perforated releasing the wetting agent. The released wetting agent would then cause the pellet 176 of dried reagents to dissolve. The wetting agents and reagents may then pass through the hole 162, and contact and wet the swabbing surface 54.

Therefore, the actuation of the perforation means causes the release of the volume of the wetting agent. The released wetting agent results in the wetting and at least partially dissolving the one or more pellets 176 provided to cause the formally dried reagent provided thereby to be carried thorough the hole 162 in the first partition wall 160 to wet the swabbing surface 54. The wetting of the swabbing surface, as discussed above, may result in at least one of a bioluminescent or a chemiluminescent assaying reaction producing the low level luminescent emissions that are detectable by the photodiode detector head assembly (if a suitable volume of analyte is present on the swabbing surface 54). It should be noted that in order to prevent the accidental actuation of the perforation means (e.g., the perforation disk 184), a lid 198 may be provided. As depicted in FIG. 9A, to actuate the perforation means, the lid 198 would be screwed off, exposing the button 194 (or an equivalent actuation structure).

As with the embodiments of FIGS. 5A and 8A, the second barrier 78, which may simply be termed 'a transparent fluid impervious barrier', may be included with detector cap assembly 30c. Although, the second barrier 78 prevents wetting agent from passing through the second opening 34b of the first portion 32, another function may be provided by the inclusion of the second barrier 78. This additional function is to prevent moisture and humidity from entering the cavity 146 by passing through the swabbing surface 54. Any moisture and humidity that enters the cavity 146 will ultimately pass through the hole 162. This should be avoided in order to keep each pellet 176 (and the reagents contained therein) completely dry and stable.

The embodiments of the detector cap assemblies 30, 30a, and 30b, which are illustrated in FIGS. 5A through 9A, are exemplary of many such possible arrangements. Other arrangements, such as those employing one or more of a variety of possible self-contained reaction vessels, may be provided by skilled persons. A possibly most preferred structure would enable standard cuvettes to be employed as 'drop-in' reaction vessels.

Figure 10:
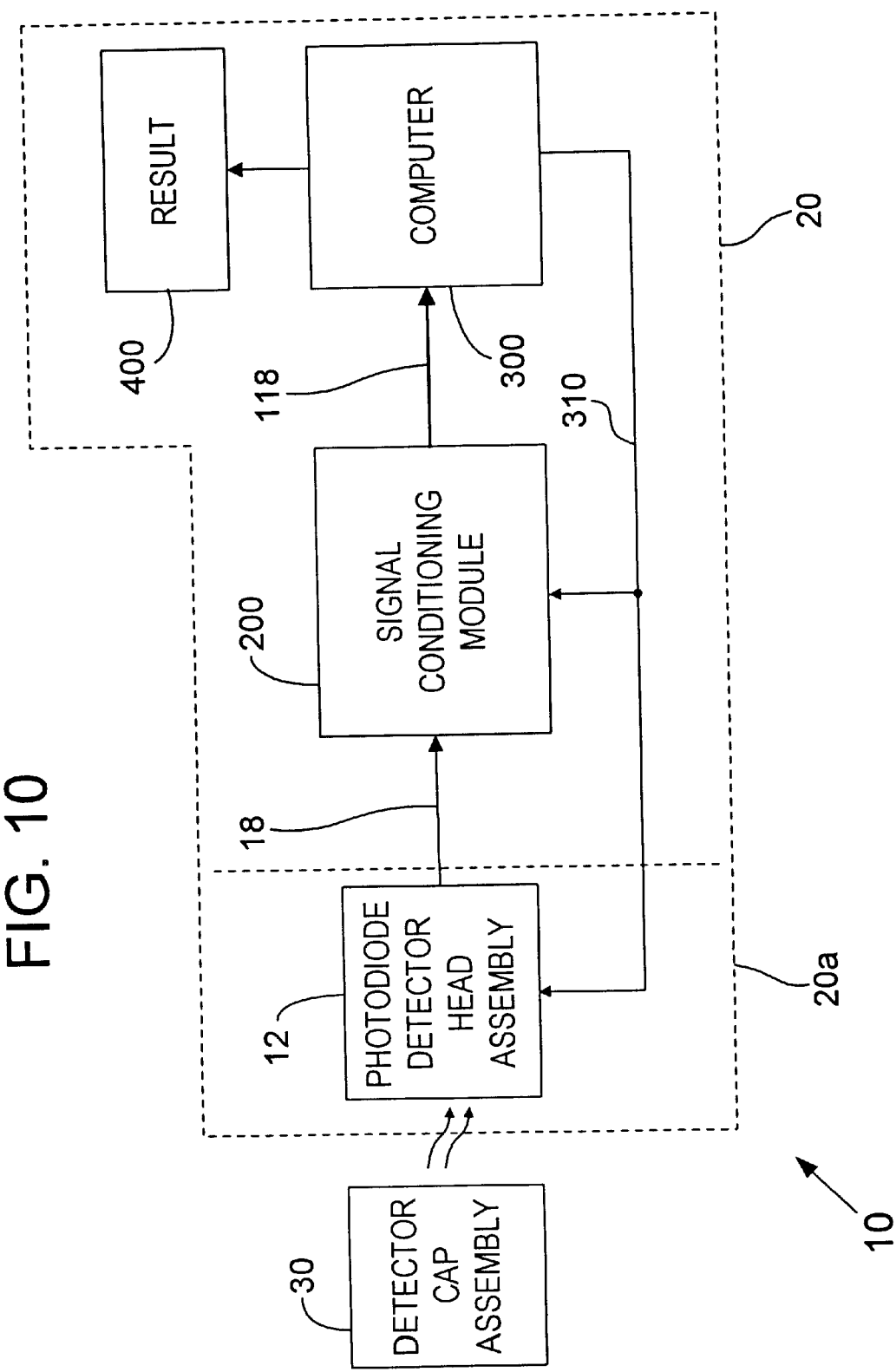
FIG. 10 provides a high-level block diagram representative of preferred embodiments of a low level luminometer in accordance with the present invention.

Referring now to FIG. 10, there is provided a high-level block diagram of preferred embodiments of a sensitive luminometer 10 and assaying arrangement in accordance with the present invention. The detector cap assembly 30, as discussed above, is configured to be removably fixed to the photodiode detector head assembly 12. The photodiode detector head assembly 12 is structured to enable the detection of the light emissions produced by at least one of a bioluminescent and or a chemiluminescent assaying reaction. The detection is indicated by at least one electrical signal 18 representative of the detected luminescent emissions produced by a suitable assay reaction. The electrical signal 18 is generated by suitable solid-state photo-electronic and electronic circuits of the photodiode detector head assembly 12. In the most preferred embodiments the luminometer 10 is housed in a hand holdable housing 20. As such, the luminometer 10 of the present invention is highly portable and fully self-contained.

A portion of the housing 20, which is structured to suitably hold the photodiode detector head assembly 12, is the detector head housing 20a. The detector head housing 20a is clearly illustrated in a preferred embodiment in FIG. 1 and FIG. 2. An important feature of the detector cap assembly 30 and the photodiode detector head assembly 12, is the placement of the source of the luminescent emissions very proximate to a photo detection means of the photodiode detector head assembly 12. This enables a source of low level emissions to be efficiently detected and quantified by the present invention. The electrical signal 18, which may be comprised of several actual analog signals, is coupled to a signal conditioning module 200. The signal conditioning module 200 receives the electrical signal 18 from the photodiode detector head assembly 12, and conditions and processes the electrical signal 18 to produce at least one digital value 118 representative of the electrical signal 18 at one or more temporal instants during a pre-determined temporal interval. Accordingly, while the bioluminescent or chemiluminescent assaying reaction is occurring the electrical signal 18 is conditioned and processed by a suitable signal conditioning module 200 to produce one or more digital values 118 that are representative of the level or strength of the emissions detected at the temporal instants during the pre-determined interval. Skilled persons will appreciate that low level emissions may be best quantified by techniques that involve the 'integration' of such a low level signal over a suitable temporal interval. Further, such integration may be proved by analog circuitry, or alternately by digital means employing hardware and or software based counting and accumulation techniques.

As can be seen in FIG. 10, a computer 300 is included in the luminometer 10 to receive and process the digital values 118 produced by the signal conditioning module 200. The computer 300 may be programmed, therefore, to collect, accumulate, and or process one or more digital values 118 to enable a result 400 to be generated that may be indicative of a level and possibly duration of the luminescent emissions detected by the detector head assembly 12. It should be noted that the signal conditioning module 200, the computer 300, and a means to provide the result 400 to a user are all contemplated in preferred embodiments as being housed within the housing 20.

It is important to note that the result 400 may be termed a 'quantified result'. For example, assume the detected luminescent emissions are produced by a bioluminescent assaying reaction, say for example, a luciferase-luciferin reaction. Then the quantified result may be indicative of a quantity of analyte that is associated with the emissions being produced. Further, the level of luminescent emissions detected and measured may be compared by the computer 300 to a pre-determined threshold level established to determine if a quantity of analyte associated with the bioluminescent assaying reaction is greater than a pre-determined quantitative limit. The pre-determined threshold level, which may be user selectable and or programmed into the computer 300, may be selected to indicate when a quantity of analyte associated with the bioluminescent assaying reaction is above an acceptable or safe limit. Accordingly, the quantitative result may simply provide a pass or fail indication. Skilled persons can provide other quantitative results that would be useful to a user or operator of the invention.

Figure 11:
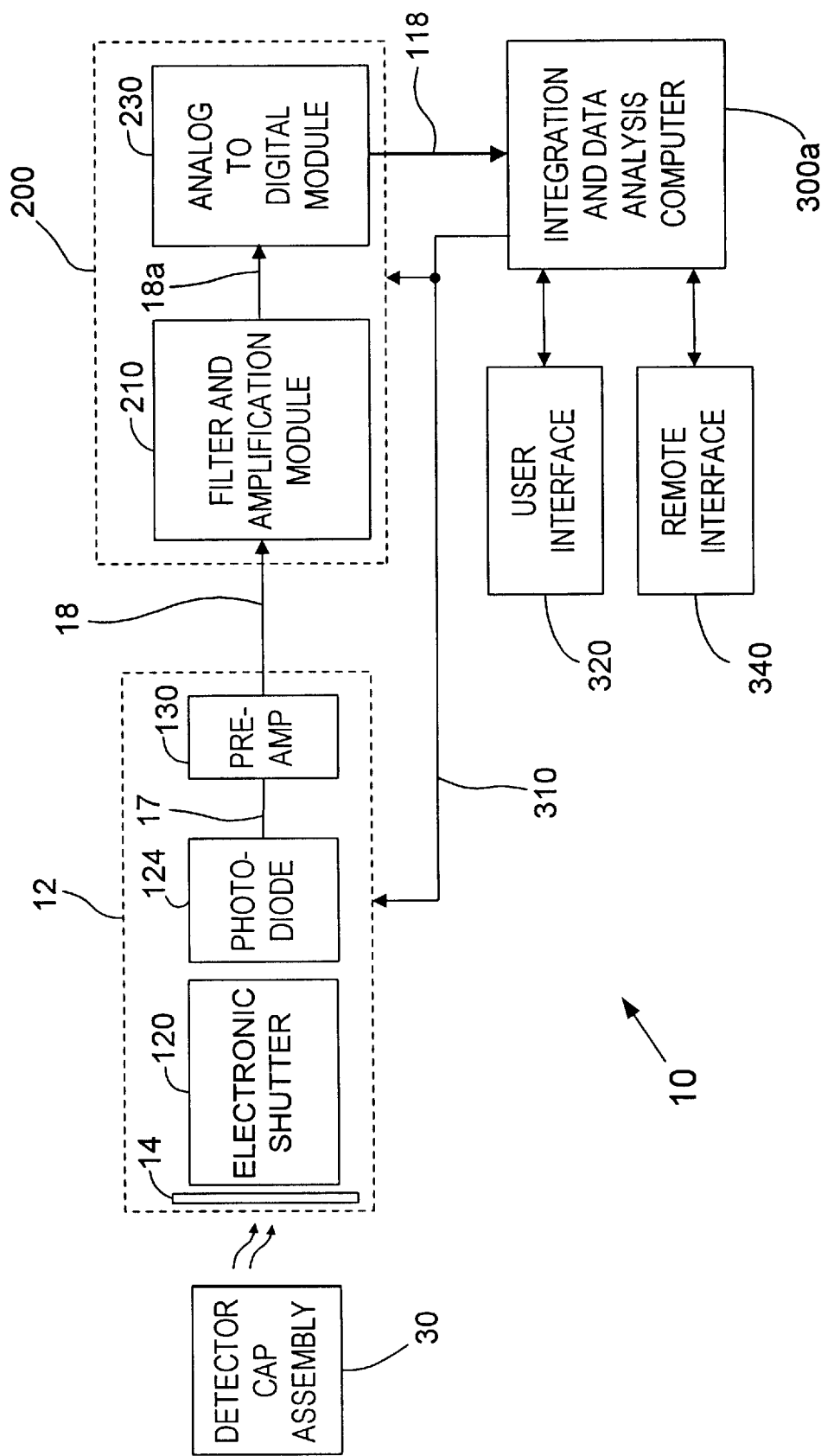
FIG. 11 is functional block diagram of a first embodiment of the luminometer.

Turning to FIG. 11, there is provided a more detailed block diagram of the assaying arrangement in accordance with the present invention. A first embodiment of the luminometer 10 includes a photodiode detector head assembly 12, a signal conditioning module 200, and an integration and data analysis computer 300a. As can be seen, the photodiode detector head assembly 12 may include an electronic shutter 120, a (semiconductor) photodiode 124, and a pre-amp 130. The photodiode 124 may be termed a 'semiconductor photodetector', or equivalently may comprise a portion of a 'photo detection means'. In a preferred embodiment of the luminometer 10 the photodiode 124 is provided by a semiconductor PIN photodiode detector. In a most preferred embodiment the photodiode 124 would be provided by a PIN photodiode 124a having a photo-detection surface area of 1–7 square milli-meters (mm) and preferably operated in a photovoltaic mode. Accordingly, the photodiode 124 may be arranged to produce a current signal 17 that is proportional to the detected low level of luminescent emissions incident upon the photodiode. The pre-amplifier 130 is provided having an input and an output. The input of the pre-amplifier 130 is coupled to the photodiode 124 to receive the current signal 17. The output of the pre-amplifier 130 produces the electrical signal 18. As such, the pre-amplifier 130 provides a higher level signal to the signal conditioning module 200 than is produced by the photodiode 124. It should be understood that the photodiode 124 and the pre-amplifier 130 may most preferably be housed in a single electronic package. The most preferred physical arrangements of the electronic shutter 120, the photodiode 124 and the pre-amplifier 130 will be further addressed when referring to FIGS. 15A and 15B.

The photodiode detector head assembly 12 may include one or more electronic shutters 120 that are responsive to the computer 300a. The electronic shutter 120 is preferably superposed over and abutting the semiconductor photodiode 124 and immediately below or behind the transparent window 14 (as shown in FIGS. 2, 6A, etc.) of the photodiode detector head assembly 12. Importantly, the window 14 is the only avenue for luminescent emissions to be incident upon and detected by the photodiode 124. The electronic shutter 120 is configured to be set to one of either a darkened state thereby significantly restricting the level of luminescent emissions incident upon the photodiode 124 and a nearly transparent state enabling available luminescent emissions to reach and be detected by the photodiode 124. The term 'significantly restricting', as applied to the level of emissions reaching the photodiode 124 when the electronic shutter 120 is in the darkened state, may be assumed to indicate that the level of emissions reaching and detected by the photodiode 124 may be reduced to a level of ¹⁄₂₀₀th to ¹⁄₄₀₀th of the level incident when the electronic shutter 120 is in the nearly transparent state. The capability to significantly reduce the level of emissions reaching the photodiode 124 is desirable for a number of reasons. First, as the luminometer 10 of the invention is constructed to be sensitive to low levels of emissions, exposure to the relatively high levels of common ambient room lighting may saturate or even damage the electronic circuits of the luminometer 10. Accordingly, when the detector cap assembly is not installed over the photodiode detector head assembly 12 (or the second portion 40 is removed from the first portion 32), it is desirable to have the computer 300*a* set the electronic shutter 120 to the darkened state. Other functions of the electronic shutter 120, which will be fully discussed below, include determining levels of dark noise prior to and or during assaying measurements and activities involving the use of the luminometer 10.

Although mechanical shutters may be employed with the present invention, the use of electronic shutters 120 reduces the mechanical complexity and the cost of construction for preferred embodiments of the photodiode detector head assembly 12. As skilled persons will appreciate, a most preferred version of the electronic shutter 120 may be provided by a polarizing liquid crystal shutter, also known as a LCD shutter. By including control bus 310 of FIGS. 10 through 13, the computer 300*a* can vary settings associated with, for example, the photodiode detector head assembly 12 and the signal conditioning module 200.

Referring again to FIG. 11, an embodiment of the signal conditioning module 200 is provided that may include a filter and amplification module 210 that receives the electrical signal 18 at its input and processes it by filtering and or amplifying the signal. The processing, which is providable by analog circuitry, may limit the bandwidth of the electrical signal 18 to minimize the noise associated with the detected luminescent emissions. A processed version of the electrical signal 18*a* is then coupled via an output of the filter and amplification module 210 to an analog-to-digital module 230 for conversion to representative digital values. The digital values 118 are then collected and processed by the computer 300*a*. The digital values 118 may be provided to the computer 300*a* by known parallel or serial digital transfer techniques. Once processing by the computer 300*a* is complete, a user interface 320 may be employed to indicate the (quantified) result 400 to a user or operator. The presented result may simply be a 'pass/fail' indication, a result calibrated in user friendly weighted scale, and or a result indicating the number of moles of analyte detected.

Figure 12:
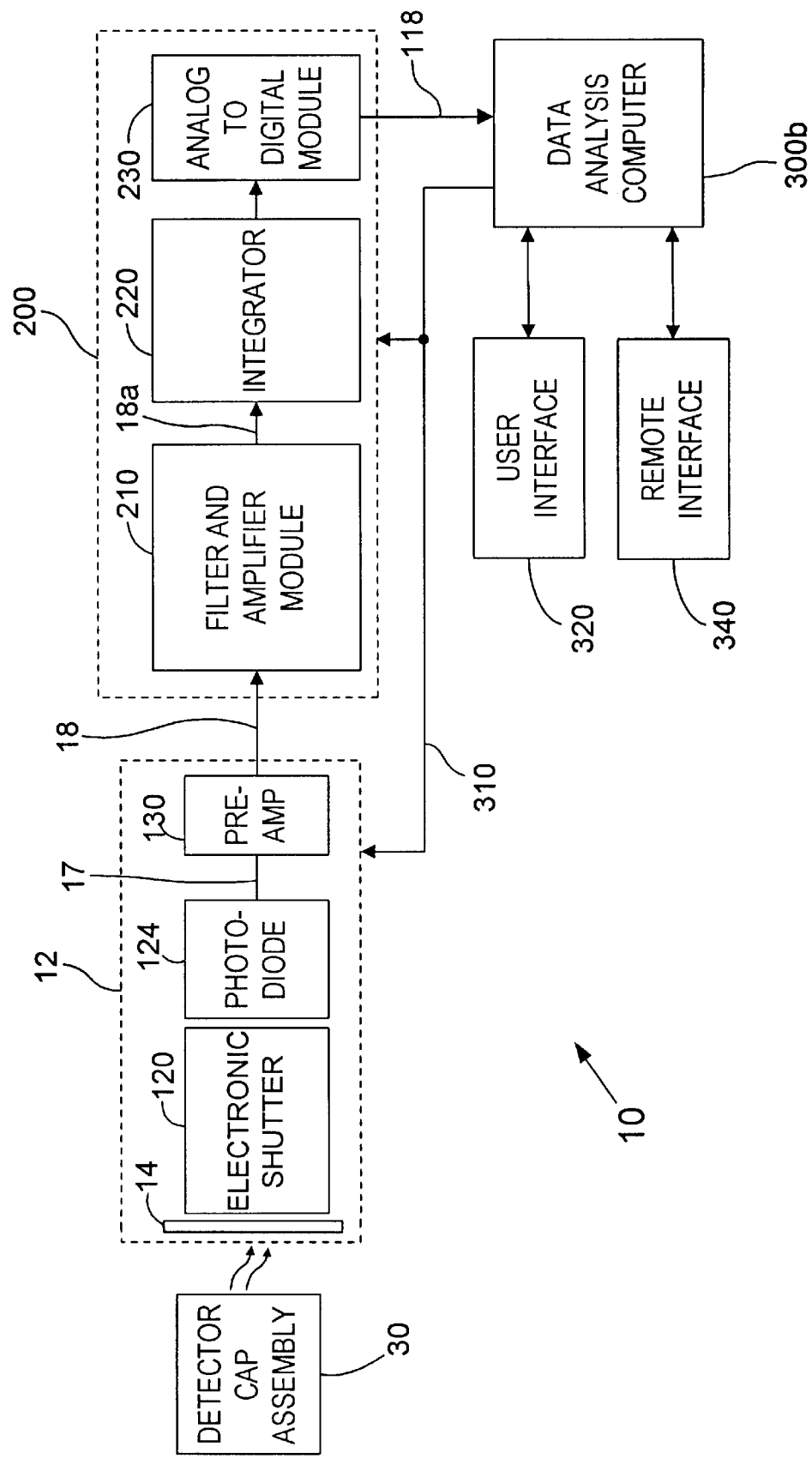
FIG. 12 is functional block diagram of another embodiment of the luminometer.

As clearly shown in FIG. 12, the signal conditioning module 200 may be modified to explicitly include an integrator 220 that is interposed between the filter and amplification module 210 and the analog-to-digital module 230. The integrator 220 includes integration circuitry provided to integrate a signal provided by the output of the filter and amplification module and produce an integrated output signal indicative of a total amount luminescent emissions detected over at least one portion of the pre-determined temporal interval. Accordingly, integrator 220 integrates the electrical signal 18*a* over a temporal interval and provides an accumulated value or total to a data analysis computer 300*b*. A application program or other suitable software of the computer 300*b*, may now omit the functions provided to integrate the digital values 118 as the integration function is now provided in the hardware of the integrator 220.

The user interface 320, which may be arranged as depicted in FIG. 1, is operatively coupled to an included computing means (e.g., computer 300 or 300*a*) and is configured to enable information to be exchanged with the user. The information exchanged may enable the user to realize or accomplish a number of actions including the inputting of gain settings to the luminometer, the calibrating of the luminometer to perform a measurement of a level of luminescent emissions associated with an assaying reaction, reset the luminometer after one measurement has been completed and before another is to begin, establish the duration of the pre-determined temporal interval during which the luminescent emissions are to be detected and measured, select one of a plurality of specific pre-determined threshold levels to be associated with a level of luminescent emissions to be determined during a respective pre-determined temporal interval, determine the power level of at least one internal rechargeable battery included within the housing, and power on and off the luminometer. In addition to the user interface 320, a remote interface 340 may be included to enable information be sent to and received from the luminometer 10/10*a*. The remote interface may include the optical port 22, which is shown in FIG. 1.

As such, the optical port 22 may be employed to enable an optical link to be established between the luminometer 10/10*a* and another instrument (such as a suitably configured personal or portable computer).

Figure 13:
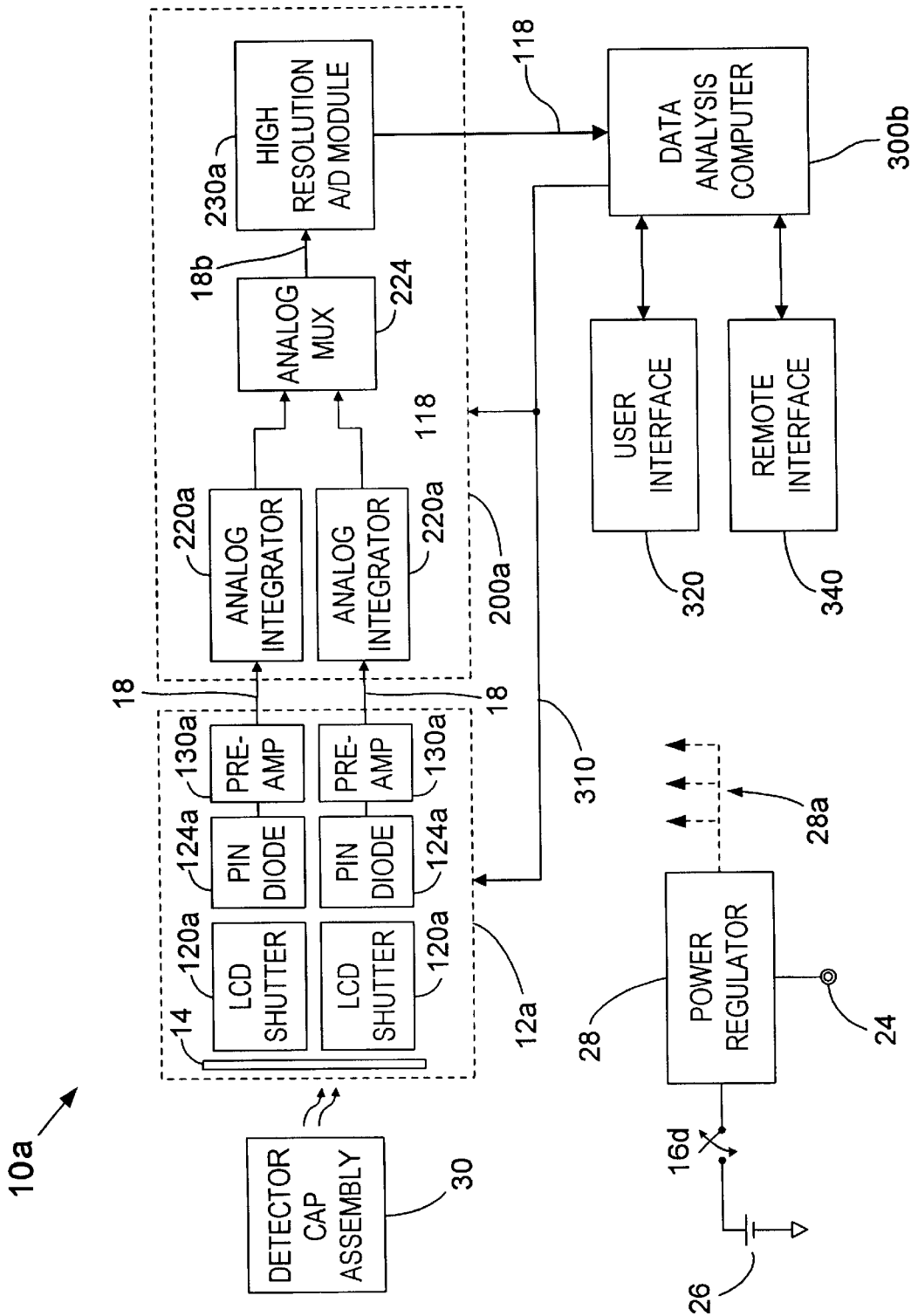
FIG. 13 provides a functional block diagram of a preferred embodiment of a multi-channel low level luminometer of the present invention.

Turning now to FIG. 13, there is illustrated a possibly most preferred embodiment of the luminometer 10 of the present invention. As illustrated, a multi-channel embodiment includes a photodiode detector head assembly 12*a*. The photodiode detector head assembly 12*a* is structured having a plurality of photodiodes and electronic shutter 120*s*. As shown, each LCD shutter 120*a* is arranged to cause a significant restriction in the level of luminescent emissions that may reach each respective photodiode. The photodiodes are most preferably provided by PIN photodiodes 124*a*. A signal conditioning module 200*a*, which may be termed a signal conditioning means, is operatively coupled to the photodiode detector head assembly 12*a* to receive, condition, and process each of a possible plurality of the electrical signals 18. As above the electrical signals 18 are processed to produce a sequence of digital values 118 representative of the electrical signals 18 over a pre-determined temporal interval. The digital values 118 may be coupled to a high resolution analog-to-digital module 230*a* via an analog multiplexer 224. The term 'high resolution' is intended to indicate that the analog-to-digital module 230*a* employed provides digital values 118 with a sufficient number of bits of resolution. For example, preferred embodiments of analog-to-digital module 230*a* may provide 18 to 20 bits of resolution. As with the embodiment of FIG. 12, a computing means may be provided such as computer 300*b*. The computer 300*b* would again be coupled to the signal conditioning module 200*a* to collect and process the sequence of digital values 118 to enable the quantified result to be generated and delivered to a user or operator.

As skilled persons will appreciate, alternate embodiments of the multi-channel arrangement provided in FIG. 13 are certainly possible. For example, the analog multiplexer 224 may be moved to receive the signals 18 from the photodiode detector head assembly 12*a*, resulting in the need for only a single analog integrator 220*a*. Other variations are certainly possible and are considered within the scope of the present invention. It is important to understand that the system structure of FIG. 13, enables a first signal that has been sampled for a pre-determined temporal sub interval to be converted by the high resolution a/d module 230a, while a second signal (say from another photo detection means) is being integrated.

The operation of the luminometers 10/10a of FIGS. 10 through 13 may be provided by a number of suitable algorithms. For example, when considering the embodiment of FIG. 11 when only one photodiode 124 is provided, it may be necessary to calibrate the luminometer 10 when the source of luminescent emissions is not active (i.e., a reaction is not occurring), possibly with the electronic shutter 120 in the darkened state. Subsequently, the assaying reaction may be started (with a suitable indication directly or indirectly provided to the computer 300a). The electronic shutter 120 would be set to the near transparent state, and the luminescent emissions from said assaying reaction would be detected and measured. An alternate measurement algorithm, which may be employed if the assaying reaction is of a sufficient temporal duration, may be summarized as follows. A series of alternating measurements of a dark signal noise level (taken with the electronic shutter 120 in the darkened state) may be collected in an interleaved fashion with measurements of the level of luminescent emissions (taken with the electronic shutter 120 in the transparent state). A system that collects a series of dark noise values and a series of actual luminescent emission values, may employ known signal processing relationships that will enable accurate measurements to be made and may enable the effects of noise changes and circuit related drifting to be greatly reduced and or eliminated.

When considering the embodiment of FIG. 13, the presence of two or more photo-channels, say with each having an electronically controlled LCD shutter 120a, enables the overlapping of measurements to be made of the dark current noise level and the level of luminescent emissions associated with the measured bioluminescent and or chemiluminescent assaying reaction. That is, a first analog integrator 220a may be integrating one signal, while an output of a second analog integrator is sampled and converted to a digital value 118. This structure enables the overlap of the integration activities with the conversion and collecting activities.

Figure 14:
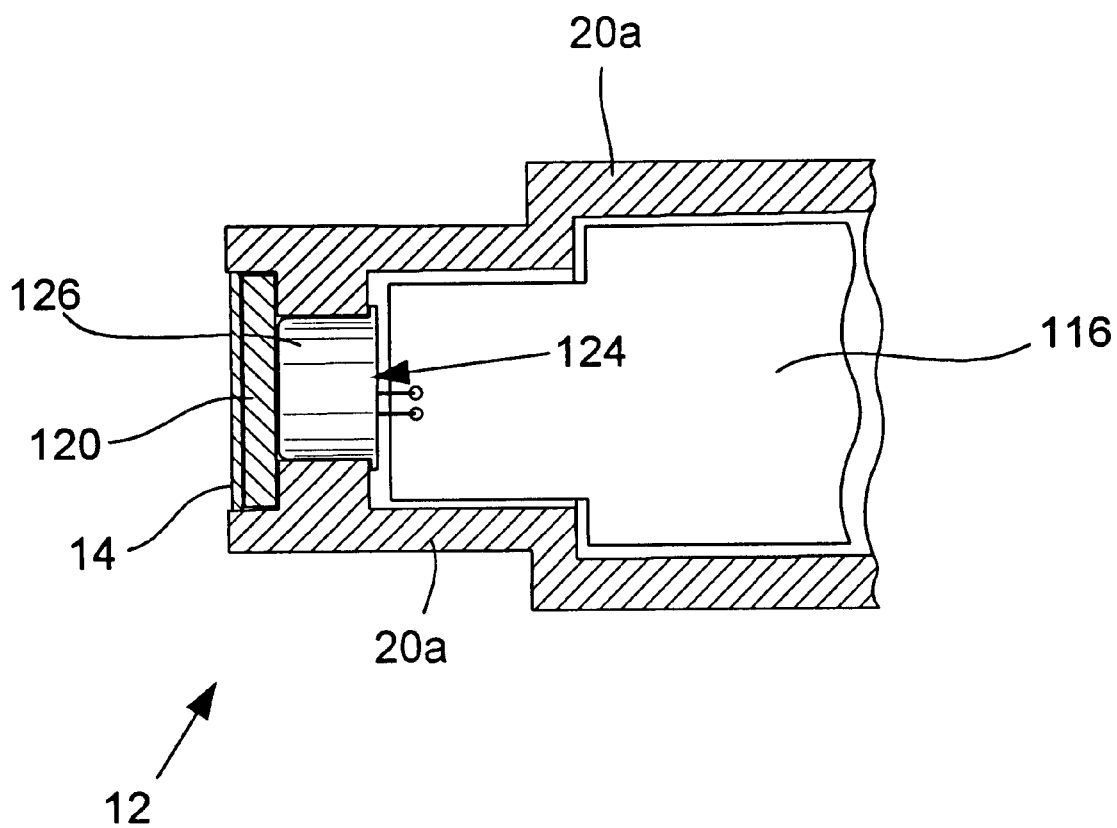
FIG. 14 provides a sectional side view of a photodiode detector head assembly that may be included with a luminometer.
Figure 15A:
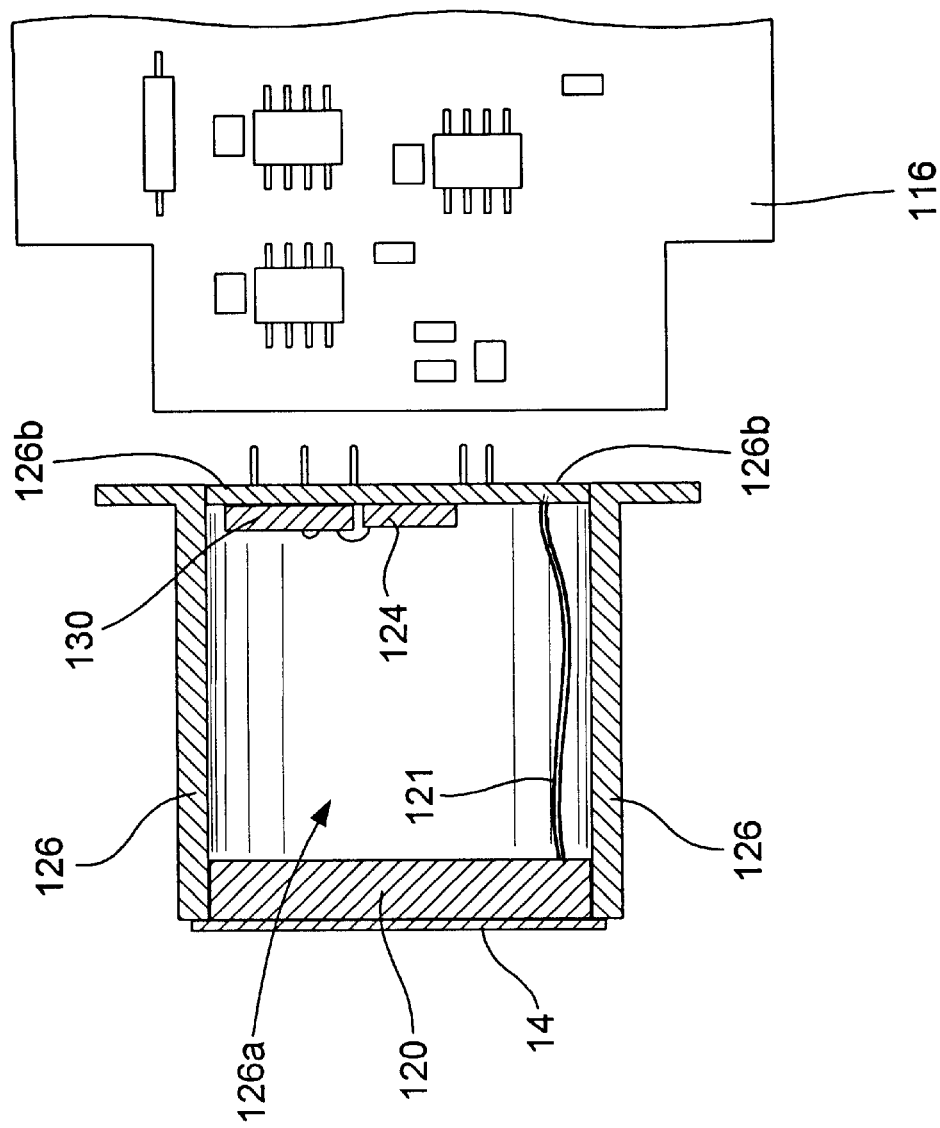
FIGS. 15A and 15B illustrate preferred embodiments of a photodiode detection device that may be employed with the photodiode detector head assembly.

Turning now to FIG. 14, there is illustrated a preferred embodiment of the photodiode detector head assembly 12. As shown, an arrangement is provided having the PIN photodiode 124a (with a window thereof) abutting and superposed by an electronic shutter 120, possibly further including a transparent window 14. A circuit board 116 may be included to provide the required electronic modules including the signal conditioning module 200, among others. As discussed above, this arrangement of components provides a photodiode detector head assembly 12 that places a photo detection means, such as a PIN photodiode 124a, in close proximity to a source of luminescent emissions. Ideally, the source of emissions would be placed superposed to and possibly abutting the left side of the transparent window 14 (as seen in FIG. 6A). A most preferred arrangement of a photodiode detector head assembly may be provided by a more integrated photo detection means as shown in FIG. 15A. As depicted, a photodetector package 126 is structured to house a photodiode 124 and a pre-amplifier 130 within a chamber 126a. The photodiode 124 and pre-amplifier 130 are preferably fixed to a base 126b of the photodetector package 126. An electronic shutter 120 is now provided in place of the standard optical window of a typical photo detection means. The arrangement of the electronic shutter 120 fixed to and mounted on the photodetector package 126 enables a distance between the photodiode 124 and a source of luminescent emissions to be reduced accordingly. Therefore, as skilled persons would appreciate, the structure depicted in FIGS. 15A and 15B, may be advantageous to the arrangement of FIG. 14. Further, it should be understood that the distance between the electronic shutter 120 and the photodiode 124, as depicted in FIGS. 15A and 15B, is illustrative only and may certainly be reduced.

Figure 15B:
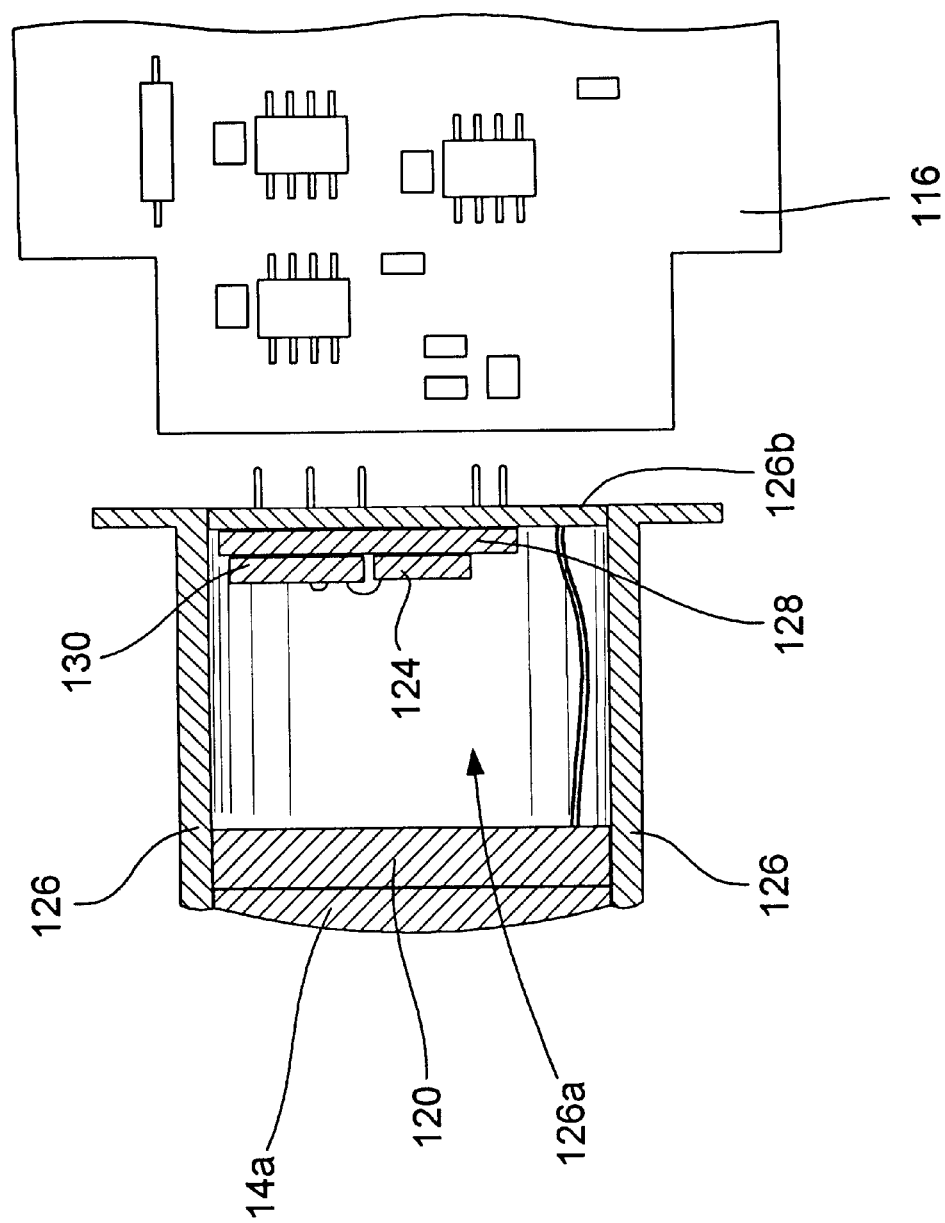

As can be seen in FIG. 15B, a thermoelectric cooler 128 may be mounted within the chamber 126a to enable the photodiode 124 and or the pre-amplifier 130 to be cooled to a suitable operating temperature. As skilled persons will understand, thermoelectric cooling elements are often employed to reduce the noise level of electronic devices and circuits. The window 14, which as depicted in FIG. 15B in a modified embodiment 14a, may be included as part of the photodetector package 126, if necessary. As shown in FIG. 15B, the window 14a may be structured to provide a function of an optical lens.

In order to not obfuscate the essential functional and operational characteristics of the various embodiments of the invention as illustrated, certain items have been omitted. For example in FIGS. 10 through 12, the inclusion of a power source, such as a (rechargeable) battery and a power regulator, have been omitted. These items, or equivalents thereof, which have been depicted in FIG. 13, may be termed an 'internal power supply', and would typically include a battery 26, an on/off switch 16a, and a power regulator 28. One or more power providing outputs 28a may be included to couple operating (e.g., bias) power to the various components of the invention. Therefore, it should be noted that an internal power supply would certainly be required with any of the disclosed preferred, self-contained, and hand holdable embodiments of the present invention. Yet other items not shown or discussed, may certainly provided with the present invention. For example, when considering FIGS. 1 through 9C, the use of threading and or bayonet mounting arrangements may be employed with the various embodiments of items that are contemplated to be removably fixed to at least one other item. Such items may include the first portion 32, the second portion 40/40', and the detector head housing 20a. As such, the presently provided descriptions are intended to be broadly define the invention, and not necessarily constrained to the explicit embodiments illustrated.

While there have been described a plurality of the currently preferred embodiments of the present invention, along with varied methods of operation, those skilled in the art will recognize that other and further modifications may be made without departing from the invention, and it is intended to claim all modifications and variations as fall within the scope of the described invention and the appended claims.

What is claimed is:

1. A self-contained assaying apparatus for use in collecting an analyte and quantifying the analyte via low levels of luminescent emissions produced by an assaying reaction, the assaying apparatus comprising:

a) a self-contained hand-holdable low level luminometer for use in detecting and quantifying low levels of luminescent emissions produced by a one of either of a bioluminescent assaying reaction and a chemiluminescent assaying reaction, the low levels of luminescent emissions produced being proportional to the quantity of analyte associated with the assaying reaction;

b) the luminometer including a photodiode detector head assembly structured with a transparent window which forms a portion of a detector head housing of a housing of the luminometer to enable the detection of the luminescent emissions entering the luminometer by way of the transparent window, the luminometer further including a computer to receive and process information operatively coupled from the photodiode detector head assembly to produce a quantified result indicative of a quantity of analyte associated with the assaying reaction;

c) a detector cap assembly structured with a swabbing surface fixed to a first portion thereof, the detector cap assembly arranged to be removably fixed to the photodiode detector head assembly forming a light tight environment so that the analyte collected on the swabbing surface of the detector cap assembly, and housed within the light tight environment, is situated directly over the transparent window and proximate to photo detection means located behind the transparent window; and d) means to cause the assaying reaction to occur within the detector cap assembly substantially upon the swabbing surface proximate to the transparent window thereby enabling the luminescent emissions produced by the assaying reaction to be detected by the photo detection means to produce a quantified result associated with the assaying reaction.

2. The assaying apparatus in accordance with claim 1, wherein the level of luminescent emissions detected and quantified is produced by a bioluminescent assaying reaction, with the level of luminescent emissions compared to a pre-determined threshold level established to determine if a quantity of analyte associated with the assaying reaction is greater than a pre-determined quantitative limit.

3. The assaying apparatus in accordance with claim 2, wherein the photodiode detector head assembly comprises:

a) a PIN photodiode that produces a current signal proportional to the detected luminescent emissions, the PIN photodiode housed within the photodiode detector head assembly and situated proximate to the transparent window; and b) a pre-amplifier having an input and an output, the input coupled to the PIN photodiode to receive the current signal produced thereby, with the output providing a higher level signal that is conditioned, processed, and coupled to the computer.

4. The luminometer in accordance with claim 3, wherein the photodiode detector head assembly further includes an electronic shutter responsive to the computer that is superposed directly over the PIN photodiode and immediately behind the transparent window of the photodiode detector head assembly, the electronic shutter structured to be set to one of either a darkened state thereby significantly restricting a level of luminescent emissions incident upon the PIN photodiode and a nearly transparent state enabling luminescent emissions to reach and be detected by the PIN photodiode.

5. The assaying arrangement in accordance with claim 1, with the detector cap assembly comprising:

a) a first portion having a wall structure providing an internal cavity, and a first opening and a second opening, the first opening and wall structure of the first portion structured to enable the first portion to be removably fixed over the photodiode detector head assembly in a light tight manner such that at least a portion of the photodiode detector head assembly substantially fills the internal cavity and so that only emissions entering the second opening of the first portion are incident upon the transparent window of the photodiode detector head assembly;

b) the swabbing surface, which is substantially flattened, pre-wetted, and is fixed to the first portion and arranged to cover the second opening thereof, the swabbing surface positioned to be superposed over the transparent window of the photodiode detector head assembly when the first portion is removably fixed over the photodiode detector head assembly in the light tight manner, the swabbing surface available to swab a surface to collect the analyte;

c) a second portion comprising a wall structure providing an internal chamber and an opening, the opening configured to enable the second portion to be removably installed onto the first portion and over the swabbing surface to cap the first portion in a light tight manner so as to substantially prevent ambient light from being incident upon the swabbing surface while the second portion is so installed thereover;

d) the second portion housing a movable structure within the chamber having a substantially flat surface that is oriented substantially parallel to a plane of the opening of the second portion, the movable structure configured to be moved between a first retracted position away from the opening of the second portion and a second deployed position more proximate to the opening;

e) a porous pad that is fixed to and substantially covering the flat surface of the movable structure, the porous pad being impregnated with suitable dried reagents that may be activated by wetting when brought into pressure contact with the pre-wetted swabbing surface; and f) a first barrier, which is thin and frangible, and arranged to cover the opening of the second portion in a recessed fashion to hermetically seal a portion of the internal chamber having the porous pad and the movable structure contained therein while the movable structure is in the first retracted position, the hermetically sealed portion of the chamber enabling the porous pad to remain dry until the first barrier is ruptured;

g) the first barrier structured to be appropriately ruptured when the movable structure is moved from the first retracted position to the second deployed position wherein the porous pad is brought into pressure contact with the swabbing surface causing the dried reagents to be drawn to and activated by the wetness of the swabbing surface possibly resulting in at least one of a bioluminescent reaction and a chemiluminescent assaying reaction producing the luminescent emissions that are detectable by the photodiode detector head assembly.

6. A self-contained luminometer for use in detecting and quantifying low levels of luminescent emissions, the luminometer comprising:

a) a photodiode detector head assembly within a detector head housing having a transparent window which forms a portion of the detector head housing of the luminometer, the detector head assembly structured with a detection means situated behind the transparent window to enable the detection of the low levels of luminescent emissions passing through the transparent window to provide an electrical signal representative thereof, the transparent window thereby arranged as a portion of the detector head housing to enable the efficient detection of the luminescent emissions entering the luminometer by way of the transparent window;

b) a signal conditioning module coupled to the detection means of the photodiode detector head assembly to receive, condition, and process the electrical signal to produce at least one digital value representative of the electrical signal at one or more temporal instants during a predetermined temporal interval; and c) a computer included to receive and process the digital values produced by the signal conditioning module to enable a quantified result to be generated indicative of a level of the luminescent emissions detected;

d) the signal conditioning module and the computer also housed within the housing, the housing structured to enable a detector cap assembly to be fixed thereto to form a light tight environment before the luminescent emissions to be detected are generated.

7. The luminometer in accordance with claim 6, wherein the photodiode detector head assembly comprises:

a) a semiconductor photodetector that produces a current signal proportional to the detected luminescent emissions; and b) a pre-amplifier having an input and an output, the input coupled to the semiconductor photodetector to receive the current signal produced thereby, with the output providing a higher level signal that is provided to the signal conditioning module.

8. The luminometer in accordance with claim 7, wherein the photodiode detector head assembly further includes an electronic shutter responsive to the computer that is superposed directly over the semiconductor photodetector and immediately behind the transparent window within the photodiode detector head assembly, the electronic shutter arranged to be set to one of either a darkened state thereby significantly restricting a level of luminescent emissions incident upon the semiconductor photodetector and a nearly transparent state enabling luminescent emissions to reach and be detected by the semiconductor photodetector.

9. The luminometer in accordance with claim 8, wherein the semiconductor photodetector is provided by a PIN photodiode arranged to detect and quantify levels of luminescent emissions that are less than 0.1 pico-watts.

10. The luminometer in accordance with claim 9, wherein the electronic shutter is provided by a polarizing liquid crystal shutter.

11. The luminometer in accordance with claim 8, wherein the signal conditioning module includes:

a) a filter and amplification module structured with an input and an output, the input coupled to the pre-amplifier to receive therefrom the electrical signal that is to be filtered, amplified, and coupled to the output; and b) an analog-to-digital converter operatively coupled to receive the output of the filter and amplification module and configured to produce at least one digital value representative of the electrical signal, which is to be communicated to the computer.

12. The luminometer in accordance with claim 11, wherein the signal conditioning module further includes an integrator interposed between the filter and amplification module and the analog-to-digital converter, the integrator provided to integrate the output of the filter and amplification module and produce an integrated output signal indicative of a total amount luminescent emissions detected over at least one portion of the pre-determined temporal interval.

13. The luminometer in accordance with claim 6, wherein the housing further houses an internal power supply and at least one rechargeable battery.

14. The luminometer in accordance with claim 10, wherein the luminescent emissions detected and quantified are produced by a bioluminescent assaying reaction, with the level of luminescent emissions compared to a pre-determined threshold level established to determine if a quantity of analyte associated with the bioluminescent assaying reaction is greater than a pre-determined quantitative limit.

15. The luminometer in accordance with claim 14, further including a user interface operatively coupled to the computer and configured to enable the quantified result to be delivered to a user.

16. The luminometer in accordance with claim 6, further including a detector cap assembly, the detector cap assembly comprising:

a) a first portion having a wall structure providing an internal cavity, and a first opening and a second opening, the first opening and wall structure of the first portion structured to enable the first portion to be removably fixed over the photodiode detector head assembly in a light tight manner such that at least a portion of the photodiode detector head assembly substantially fills the internal cavity and so that only emissions entering the second opening of the first portion are incident upon and pass through the transparent window of the photodiode detector head assembly;

b) a substantially flattened and pre-wetted swabbing surface that is fixed to the first portion and arranged to cover the second opening thereof, the swabbing surface positioned to be superposed over the transparent window of the photodiode detector head assembly when the first portion is removably fixed over the photodiode detector head assembly in the light tight manner, and available to swab a surface to collect analyte;

c) a second portion having a wall structure providing an internal chamber and an opening, the opening configured to enable the second portion to be removably installed onto the first portion to cap the swabbing surface in a light tight manner so as to substantially prevent ambient light from being incident upon the swabbing surface while the second portion is so installed thereover;

d) the second portion housing a movable structure within the internal chamber having a flat surface that is oriented parallel to the plane of the swabbing surface, the movable structure configured to be moved between a first retracted position spaced from the opening of the second portion and a second deployed position more proximate to the opening;

e) a porous pad that is fixed to and substantially covering the flat surface of the movable structure, the porous pad being impregnated with suitable dried reagents that may be activated by wetting when brought into pressure contact with the pre-wetted swabbing surface; and f) a first barrier, which is thin and frangible, and arranged to cover the opening of the second portion in a recessed fashion to hermetically seal a portion of the internal chamber having the porous pad and the movable structure contained therein while the movable structure is in the first retracted position, the hermetically sealed portion of the chamber enabling the porous pad to remain dry until the first barrier is ruptured;

g) the first barrier structured to be appropriately ruptured when the movable structure is moved from the first retracted position to the second deployed position causing the porous pad to be brought into pressure contact with the swabbing surface causing the dried reagents to be drawn to and activated by the wetness of the swabbing surface, possibly resulting in at least one of a bioluminescent reaction and a chemiluminescent assaying reaction producing the luminescent emissions that are detectable by the photodiode detector head assembly.

17. The luminometer in accordance with claim 16, further including a transparent fluid impervious second barrier provided under the swabbing surface and over the second opening of the first portion to seal the second opening to prevent the transport of moisture therethrough.

18. The luminometer in accordance with claim 17, wherein the swabbing surface is pre-wetted with a volume of wetting agents comprising:
 a) sterile water;
 b) a nucleotide releasing reagent; and optionally
 c) buffering agents.

19. The luminometer in accordance with claim 18, wherein the swabbing surface includes at least one of:
 a) a cotton pad; and
 b) a polymer pad.

20. The luminometer in accordance with claim 19, wherein the porous pad is comprised of a plurality of layers.

21. The luminometer in accordance with claim 16, wherein the second portion is comprised of:
 a) an outer cap-like portion having a cylindrical wall structure, with an interior surface of the cylindrical wall structure having formed therein a spiral groove, the cap-like portion coaxially and coextensively disposed over a cylindrical wall structure of the second portion and rotatably fixed thereto to enable rotation around a center axis of each of the outer cap-like portion and the wall structure of the second portion;
 b) the cylindrical wall structure of the second portion having at least one slot formed therein extending parallel to the center axis thereof;
 c) the movable structure of the detector cap assembly structured with a substantially cylindrical shape having at least one raised block with an angled follower tab extending radially therefrom, the raised block structured to fit into and slide up and down the slot while the angled follower tab is arranged to extend through the slot and mate to and follow the spiral groove of the cap-like portion;
 d) the movable structure configured to be movable from the first retracted position to the second deployed position by rotating the outer cap-like portion with respect to the second portion.

22. The luminometer in accordance with claim 16, wherein the second portion comprises:
 a) an outer cap-like portion having a cylindrical wall structure closed by a top surface at a first end and open at a second end, the cylindrical wall structure of the outer cap-like portion having a threaded portion provided on an inner surface thereof, the outer cap-like portion configured to be initially at least partially coextensively disposed over a cylindrical wall structure of the second portion and coaxially aligned therewith;
 b) the cylindrical wall structure of the second portion having a first end proximate to the opening and a second end, wherein an outer surface of the cylindrical wall structure of the second portion is configured with a treaded portion situated proximate to the second end that is structured to mate and engage the threaded portion of the outer cap-like portion, the engaged respective threaded portions enabling the outer cap-like portion to move along a common center axis of each of the second portion and the outer cap-like portion when the outer cap-like portion is rotated around the center axis with respect to the second portion, said rotation causing the outer cap-like portion to be screwed coextensively and coaxially down and over the second portion;
 c) the outer cap-like portion further having the movable structure fixed to the top surface and substantially axially aligned with the outer cap-like portion, the movable structure extending down into the second portion with the movable structure movable from the first retracted position to the second deployed position when the outer cap-like portion is rotated and screwed down over the second portion, thereby causing the frangible first barrier to be ruptured and to place the porous material in pressure contact with the pre-wetted swabbing surface.

23. The luminometer in accordance with claim 22, wherein the cap-like portion is secured from rotating with respect to the second portion by a safety locking means that is removed after swabbing activities have occurred to enable the movable structure to be moved from the first retracted position to the second deployed position by the rotating of the outer cap-like portion around the center axis with respect to the second portion.

24. A self-contained low level luminometer for use in detecting and quantifying low levels of visible light emissions produced by one of either of a bioluminescent and a chemiluminescent assaying reaction, the luminometer comprising:
 a) a photodiode detector head assembly configured with a transparent window which forms a portion of a detector head housing of the luminometer, the detector head assembly structured to enable the detection of the light emissions that pass through the transparent window by photodiode detection means located behind the transparent window within the detector head housing to provide at least one electrical signal representative thereof;
 b) signal conditioning means operatively coupled to the photodiode detection means of the photodiode detector head assembly to receive, condition, and process the electrical signals to produce a sequence of digital values representative of the electrical signals over a predetermined temporal interval; and
 c) computing means coupled to the signal conditioning means and structured to collect and process the sequence of digital values to enable a quantified result to be delivered to a user that is associated with the level of visible light emissions produced by the assaying reaction;
 d) the signal conditioning means and the computing means suitably mounted within the housing, with the housing structured to enable a detector cap assembly to be fixed thereto to form a light tight environment wherein the light emissions to be detected may be generated in the absence of ambient light.

25. The low level luminometer in accordance with claim 24, wherein the level of visible light emissions detected and quantified is produced by a bioluminescent assaying reaction, with said level of visible light emissions compared to a pre-determined threshold level established to determine if a quantity of analyte associated with the bioluminescent assaying reaction is in excess of a pre-determined quantitative limit.

26. The low level luminometer in accordance with claim 25, further including a user interface operatively coupled to the computing means and configured to enable the quantified result to be delivered to a user, the result including an indication of at least one of:
   a) if the level of visible light detected is in excess of the pre-determined threshold level; and
   b) if a quantity of analyte associated with the bioluminescent assaying reaction is in excess of the pre-determined quantitative limit.

27. The low level luminometer in accordance with claim 24, wherein the photodiode detector head assembly comprises:
   a) at least one semiconductor photodetector that is arranged to detect the level of the visible light emissions and produce at least one signal proportional thereto; and
   b) a pre-amplifier coupled to each semiconductor photodetector to receive the respective signals therefrom and produce each respective electrical signal that is coupled to the signal conditioning means.

28. The low level luminometer in accordance with claim 27, wherein each semiconductor photodetector is provided by a PIN photodiode.

29. The low level luminometer in accordance with claim 28, wherein the photodiode detector head assembly further includes at least one electronic shutter that is responsive to the computer means, each electronic shutter suitably positioned and configured to be set to one of either a darkened state thereby significantly restricting the level of visible light emissions incident upon a respective PIN photodiode and a nearly transparent state enabling visible light emissions to be incident upon the respective PIN photodiode.

30. The low level luminometer in accordance with claim 28, wherein the signal conditioning means includes:
   a) a filter and amplification module structured with an input and an output, the input suitably coupled to the pre-amplifier to receive therefrom the electrical signal; and
   b) an analog-to-digital converter coupled to the output of the filter and amplification module and configured to produce the sequence of digital values over the predetermined temporal interval.

31. The low level luminometer in accordance with claim 28, wherein the signal conditioning means includes:
   a) a filter and amplification module structured with an input and an output, the input coupled to the pre-amplifier to receive therefrom the electrical signal;
   b) an integrator coupled to the output of the filter and amplification module and structured to integrate a filtered and amplified signal, which is proportional to the electrical signal provided from the pre-amplifier, the integrator producing an integrated output signal indicative of a total amount of visible light emissions detected over the pre-determined temporal interval; and
   c) an analog-to-digital converter operatively coupled to the integrated output signal to produce at least one digital value representative of the integrated output signal.

32. The low level luminometer in accordance with claim 28, wherein the signal conditioning means provides a multichannel signal conditioning means comprising:
   a) an analog integrator for each respective PIN photodiode, each analog integrator structured with an input and an output, with each input coupled to a respective pre-amplifier to receive therefrom the electrical signal, and each output producing an integrated output signal indicative of a total amount of visible light emissions measured over a pre-determined temporal interval by an associated PIN photodiode;
   b) an analog multiplexer for receiving each integrated output signal of the analog integrators and enabling a selected output of the analog integrators to be coupled to a high resolution analog-to-digital converter;
   c) the analog-to-digital converter activated to produce at least one digital value for each integrated output signal provided to the analog multiplexer.

33. The low level luminometer in accordance with claim 32, wherein at least two channels provided by the analog multiplexer are employed to alternately sample associated integrated output signals, the associated output signals produced by alternate measurements conducted with the electronic shutter first in the darkened state and subsequently in the transparent state, wherein the measurements made in the darkened state are indicative of a dark current noise level of the PIN photodiode, while measurements made in the transparent state are indicative of the level of visible light emissions detected.

34. The low level luminometer in accordance with claim 24, wherein the housing further contains an internal power supply that includes at least one rechargeable battery.

35. The low level luminometer in accordance with claim 24, further including a user interface operatively coupled to the computing means and configured to enable information to be exchanged with the user, the information exchanged enabling the user to accomplish at least one of the following:
   a) input gain settings to the luminometer;
   b) calibrate the luminometer to perform a measurement of the level of visible light emissions associated with an assaying reaction;
   c) reset the luminometer after one measurement of the level of visible light emissions has been made and before another is to begin;
   d) establish a duration of the pre-determined temporal interval during which visible light emissions produced by the bioluminescent or the chemiluminescent assaying reaction are to be detected;
   e) select one of a plurality of specific pre-determined threshold levels associated with a level of visible light emissions to be determined during the predetermined temporal interval;
   f) determine the power level of at least one internal rechargeable battery included within the housing; and
   g) power on and off the luminometer.

36. A detector cap assembly structured for use with a low level luminometer including a photodiode detector head assembly, the detector cap assembly comprising:
   a) a first portion including a wall structure providing an internal cavity and having a first opening and a second opening, the first opening and wall structure of the first portion structured to enable the first portion to be removably fixed over the photodiode detector head assembly in a light tight manner such that a portion of the photodiode detector head assembly substantially fills the internal cavity so as to place photo detection means thereof in a position proximate to the second opening so that only luminescent emissions entering the second opening of the first portion are incident upon the photo detection means of the photodiode detector head assembly;

b) a substantially flattened and pre-wetted bibulous swabbing surface that is fixed to the first portion and arranged to cover the second opening thereof, the swabbing surface, which is positioned so as to be superposed over the photo detection means when the first portion is removably fixed over the photodiode detector head assembly in the light tight manner, available to swab a surface to collect analyte;

c) a second portion having a wall structure providing an internal chamber and an opening, the opening configured to enable the second portion to be removably installed onto the first portion to cap the first portion in a light tight manner so as to prevent any ambient light from being incident upon the swabbing surface while the second portion is installed thereover;

d) the second portion housing a movable structure within the chamber having a flat surface that is oriented substantially parallel to the plane of the swabbing surface, the movable structure configured to be movable between a first retracted position away from the opening of the second portion and a second deployed position more proximate to the opening;

e) a porous pad fixed to and substantially covering the flat surface of the movable structure, the porous pad being impregnated with suitable dried reagents that may be activated by wetting when brought into pressure contact with the pre-wetted swabbing surface; and f) a barrier means, which is thin and frangible, and arranged to cover the opening of the second portion in a recessed fashion to hermetically seal a portion of the internal chamber having the porous pad and the movable structure contained therein while the movable structure is in the first retracted position, the hermetically sealed portion of the chamber enabling the porous pad to remain dry until the barrier means is ruptured;

g) the barrier means structured to be appropriately ruptured when the movable structure is moved from the first retracted position to the second deployed position wherein the porous pad is brought into pressure contact with the swabbing surface causing the dried reagents to be drawn to and activated by the wetness of the swabbing surface, possibly resulting in at least one of a bioluminescent and a chemiluminescent assaying reaction producing the luminescent emissions that are detectable by the photo detection means of the photodiode detector head assembly.

37. The detector cap assembly in accordance with claim 36, further including a transparent fluid impervious barrier interposed under the swabbing surface and over the second opening of the first portion to seal the second opening to prevent the transport of moisture therethrough.

38. The detector cap assembly in accordance with claim 37, wherein the swabbing surface is pre-wetted with a volume of wetting agent comprising:

a) sterile water;

b) a nucleotide releasing reagent; and optionally c) buffering agents.

39. The detector cap assembly in accordance with claim 38, wherein the swabbing surface is comprised of at least one of:

a) a cotton pad; and b) a polymer pad.

40. The detector cap assembly in accordance with claim 38, wherein the porous pad is provided by a porous polymer sheet material.

41. The detector cap assembly in accordance with claim 36, wherein the second portion is comprised of:

a) an outer cap-like portion having a cylindrical wall structure with an interior surface of the cylindrical wall structure having formed therein a spiral groove, the cap-like portion coaxially and coextensively disposed over a cylindrical wall structure of the second portion and structured to be rotatably fixed thereto to enable rotation around a center axis of each of the outer cap-like portion and the cylindrical wall structure of the second portion;

b) the cylindrical wall structure of the second portion having at least one slot formed therein extending parallel to the center axis;

c) the movable structure of the detector cap assembly structured with a substantially cylindrical shape having at least one raised block with an angled follower tab extending radially therefrom, the raised block structured to fit into and slide up and down the slot while the angled follower tab is arranged to extend through the slot and mate to and follow the spiral groove of the cap-like portion;

d) the movable structure configured to be movable from the first retracted position to the second deployed position by rotating the outer cap-like portion with respect to the second portion.

42. The detector cap assembly in accordance with claim 36, wherein the second portion is comprised of:

a) an outer cap-like portion having a cylindrical wall structure closed by a top surface at a first end and open at a second end, the cylindrical wall structure having a threaded portion provided on an inner surface thereof, the outer cap-like portion configured to be initially at least partially coextensively disposed over a cylindrical wall structure of the second portion and coaxially aligned therewith;

b) the cylindrical wall structure of the second portion having a first end proximate to the open end and a second end, wherein an outer surface of the cylindrical wall structure of the second portion is configured with a treaded portion situated proximate to the second end that is structured to mate and engage the threaded portion of the outer cap-like portion, the respective engaged threaded portions enabling the outer cap-like portion to move along a common center axis of each of the second portion and the outer cap-like portion when the outer cap-like portion is rotated (around the center axis) with respect to the second portion, said rotation causing the outer cap-like portion to be screwed coaxially and coextensively down and over the second portion;

c) the outer cap-like portion further having the movable structure fixed to the top surface and substantially axially aligned with the outer cap-like portion, the movable structure extending down into the second portion with the movable structure movable from the first retracted position to the second deployed position when the outer cap-like portion is rotated and screwed down over the cylindrical wall structure of the second portion, thereby causing the frangible first barrier to be ruptured and to place the porous material in pressure contact with the swabbing surface.

43. A detector cap assembly structured for use with a hand holdable self-contained luminometer having a photodiode detector head assembly configured to detect low level luminescent emissions, the detector cap assembly comprising:

a) a first portion including a wall structure providing an internal cavity and including a first opening and a second opening, the first opening and wall structure of the first portion structured to enable the first portion to be removably fixed over the photodiode detector head assembly in a light tight manner such that the photodiode detector head assembly substantially fills a portion of the cavity so as to place photo detection means thereof in a suitable position proximate to the second opening so that only luminescent emissions entering the second opening of the first portion are incident upon the photo detection means of the photodiode detector head assembly;

b) a substantially flattened swabbing surface, which is available to swab a surface to collect analyte, is fixed to the first portion and arranged to cover the second opening thereof, the swabbing surface positioned so as to be superposed over the photo detection means when the first portion is removably fixed over the photodiode detector head assembly in the light tight manner, c) a second portion having an outer wall structure, a top end and a bottom end, the second portion configured with a top opening at the top end and a bottom opening at the bottom end, the bottom opening arranged to enable the second portion to be removably installed onto the first portion to cap the first portion and the swabbing surface in a light tight manner so as to prevent any ambient light from being incident upon the swabbing surface while the second portion so installed thereover;

d) a first partition wall oriented substantially traverse to the bottom opening and within the wall structure of the second portion so as to form a cavity proximate to the bottom opening, the first partition wall having at least one hole located therein;

e) a second partition wall oriented substantially traverse to the top opening and within the wall structure of the second portion so as to form a chamber that is situated above the cavity proximate to the bottom opening, the second partition wall having a hole provided therein;

f) a sealed fluid holding envelope situated in the chamber, the fluid holding envelope filled with a suitable volume of wetting agent;

g) perforation means structured to be actuated from a location proximate to the top opening, above the second partition wall, the perforation means substantially housed within the chamber and arranged to perforate the fluid holding envelope in order to release the volume of wetting agent into the chamber; and h) at least one pellet of dried reagent that is situated between the fluid holding envelope and a top surface of the first partition wall, the pellets sized having a diameter greater than each hole provided in the first partition wall so that the pellets will not easily move through the respective holes;

i) the activation of the perforation means causing a release of the volume of wetting agent contained in the fluid holding envelope, thereby wetting and at least partially dissolving the pellets to cause the dried reagent provided thereby to be carried thorough the holes in the first partition wall to wet the swabbing surface, possibly resulting in at least one of a bioluminescent and a chemiluminescent assaying reaction producing the low level luminescent emissions that are detectable by the photo detection means of the photodiode detector head assembly.

44. The detector cap assembly in accordance with claim 43, wherein in the first partition wall is configured with a substantially concaved shape.

45. The detector cap assembly in accordance with claim 44, further including a transparent fluid impervious barrier interposed under the swabbing surface and over the second opening of the first portion to seal the second opening to prevent the transport of moisture therethrough.

46. The detector cap assembly in accordance with claim 43 wherein the perforation means comprises:

a) a perforation disk located in the chamber above the fluid holding envelope and structured with a first surface and a second surface, the first surface having with a plurality of piercing points extending therefrom, the first surface oriented parallel to and spaced from the fluid holding envelope when the perforation means is not actuated; and b) a shaft having a first end and a second end, the first end fixed to the second surface of the perforation disk and configured so that the shaft passes through the hole in the second partition wall with the second end of the shaft situated at the location proximate to the top opening above the second partition wall and available to actuate the perforation means by moving the perforation disk from a first position with the perforation disk spaced from the fluid holding envelope to a second position with the perforation disk perforating the fluid holding envelope thereby releasing the volume of wetting agent.

47. The detector cap assembly in accordance with claim 46, further including a button fixed to second end of the shaft to assist in activating the perforation means.

48. The detector cap assembly in accordance with claim 46, further including a lid to prevent the accidental actuation of the perforation means.

49. The detector cap assembly in accordance with claim 43, wherein the swabbing surface is provided by a polymer pad.

50. The detector cap assembly in accordance with claim 49, wherein the fluid contained within the fluid holding envelope includes:

a) sterile water;
b) a nucleotide releasing reagent; and optionally
c) buffering agents.

* * * * *